US010012654B2

(12) United States Patent
Florholmen et al.

(10) Patent No.: US 10,012,654 B2
(45) Date of Patent: Jul. 3, 2018

(54) BIOMARKERS IN INFLAMMATORY BOWEL DISEASE

(71) Applicant: University of Tromsø, Tromsø (NO)

(72) Inventors: Jon Florholmen, Tromsø (NO); Trine Olsen, Tromsø (NO); Renathe Rismo, Tromsø (NO); Rasmus Goll, Tromsø (NO); Guanglin Cui, Tromsø (NO)

(73) Assignee: UNIVERSITY OF TROMSØ, Tromsø (NO)

( * ) Notice: Subject to any disclaimer, the term of this patent is extended or adjusted under 35 U.S.C. 154(b) by 0 days.

(21) Appl. No.: 14/653,750

(22) PCT Filed: Dec. 23, 2013

(86) PCT No.: PCT/GB2013/053418
§ 371 (c)(1),
(2) Date: Jun. 18, 2015

(87) PCT Pub. No.: WO2014/096873
PCT Pub. Date: Jun. 26, 2014

(65) Prior Publication Data
US 2015/0323546 A1 Nov. 12, 2015

(30) Foreign Application Priority Data
Dec. 21, 2012 (GB) .................................. 1223223.7

(51) Int. Cl.
| | | |
|---|---|---|
| *C12Q 1/68* | (2018.01) | |
| *G01N 33/00* | (2006.01) | |
| *A61K 39/00* | (2006.01) | |
| *G01N 33/566* | (2006.01) | |
| *G01N 33/68* | (2006.01) | |
| *C12Q 1/6883* | (2018.01) | |
| *G06F 19/00* | (2018.01) | |
| *G01N 33/50* | (2006.01) | |

(52) U.S. Cl.
CPC ....... *G01N 33/6863* (2013.01); *C12Q 1/6883* (2013.01); *G01N 33/5088* (2013.01); *G01N 33/6893* (2013.01); *G06F 19/345* (2013.01); *C12Q 2600/106* (2013.01); *C12Q 2600/158* (2013.01); *G01N 2333/525* (2013.01); *G01N 2333/54* (2013.01); *G01N 2333/57* (2013.01); *G01N 2800/065* (2013.01); *G01N 2800/52* (2013.01); *G01N 2800/54* (2013.01); *G01N 2800/56* (2013.01)

(58) Field of Classification Search
None
See application file for complete search history.

(56) References Cited

U.S. PATENT DOCUMENTS

| | | |
|---|---|---|
| 6,001,569 A | 12/1999 | Plevy et al. |
| 6,183,951 B1 | 2/2001 | Plevy et al. |
| 2004/0219555 A1 | 11/2004 | Van Heel |
| 2006/0205012 A1 | 9/2006 | DeBad et al. |
| 2006/0216716 A1 | 9/2006 | Saubermann et al. |
| 2011/0081649 A1 | 4/2011 | Thoern et al. |
| 2012/0094289 A1 | 4/2012 | Garrity-Park et al. |

FOREIGN PATENT DOCUMENTS

| | | |
|---|---|---|
| EP | 0760010 | 3/1997 |
| JP | H0313864 | 1/1991 |
| RU | 2258223 | 8/2005 |
| WO | 1997/039146 | 10/1997 |
| WO | 2005/029091 | 3/2005 |
| WO | 2010/062663 | 6/2010 |
| WO | 2010/062960 | 6/2010 |
| WO | 2010/085658 | 7/2010 |
| WO | 2010/103350 | 9/2010 |
| WO | 2013/080050 | 6/2013 |

OTHER PUBLICATIONS

Best, W.R., et al., "Development of a Crohn's Disease Activity Index," Gastroenterology, vol. 70, No. 3, 1976, pp. 439-444.
Cooney, R.M., et al., "Outcome measurement in clinical trials for ulcerative colitis: towards standardization," Trials, vol. 8, No. 17, 2007, 9 pages.
D'Haens, G., et al., "A Review of Activity Indices and Efficacy End Points for Clinical Trials of Medical Therapy in Adults With Ulcerative Colitis," Gastroenterology, vol. 132, 2007, pp. 763-786.
Daperno, M., et al., "Development and validation of a new, simplified endoscopic activity score for Crohn's disease: the SES-CD," Gastrointestinal Endoscopy, 2004, vol. 60, No. 4, pp. 505-512.
Daperno, M., et al., "Results of the 2nd part Scientific Workshop of the ECCO. II: Measures and markers of prediction to achieve, detect, and monitor intestinal healing in inflammatory bowel disease," Journal of Crohn's and Colitis, vol. 5, 2011, pp. 484-498.
Florholmen, J., et al., "Candidate mucosal and surrogate biomarkers of inflammatory bowel disease in the era of new technology," Scandinavian Journal of Gastroenterology, vol. 46, Issue 12, 2011, pp. 1407-1417.
Harvey, R.F., et al., "A Simple Index of Crohn's-Disease Activity," The Lancet, vol. 315, No. 8167, 1980, p. 514.
Hassan, C., et al., "Tumour necrosis factor alpha down-regulation parallels inflammatory regression in ulcerative colitis patients treated with infliximab," Digestive and Liver Disease, vol. 39, 2007, pp. 811-817.

(Continued)

*Primary Examiner* — Vanessa L . Ford
*Assistant Examiner* — Jegatheesan Seharaseyon
(74) *Attorney, Agent, or Firm* — Meunier Carlin & Curfman LLC

(57) ABSTRACT

The present invention provides a method of determining whether a patient with inflammatory bowel disease (IBD) and who has been treated with anti TNFα therapy is in immunological remission (IR), said method comprising determining the level of a cytokine selected from TNFα, IL-17 and IFN-y in a Gl mucosal sample from said patient. Also provided are methods of prognosis and treatment using said method of determination, in particular discontinuing treatment if said patient is in IR and continuing treatment if said patient is not in IR.

13 Claims, 5 Drawing Sheets

(56) References Cited

OTHER PUBLICATIONS

Irvine, E., et al., "Quality of Life: A Valid and Reliable Measure of Therapeutic Efficacy in the Treatment of Inflammatory Bowel Disease," Gastroenterology, vol. 106, No. 2, 1994, pp. 287-296.

Liu, Z., et al., "Blockage of tumor necrosis factor prevents intestinal mucosal inflammation through down-regulation of interleukin-23 secretion," Journal of Autoimmunity, vol. 29, 2007, pp. 187-194.

Ljung, T., et al., "Early changes in rectal nitric oxide and mucosal inflammatory mediators in Crohn's colitis in response to infliximab treatment," Alimentary Pharmacology & Therapeutics, vol. 25, 2007, pp. 925-932.

Meucci, G., et al., "Prognostic Significance of Endoscopic Remission in Patients with Active Ulcerative Colitis Treated with Oral and Topical Mesalazine: A Prospective, Multicenter Study," Inflammatory Bowel Disease, vol. 18, No. 6, 2012, pp. 1006-1010.

National Institute for Health and Care Excellence (NICE), "Infliximab and adalimumab for the treatment of Crohn's disease," Technology appraisal guidance, retrieved from the Internet at http://guidance.nice.org.uk/TA187, 2010, 41 pages.

Olsen, T., et al., "Infliximab therapy decreases the levels of TNF-$\alpha$ and IFN-$\gamma$ mRNA in colonic mucosa of ulcerative colitis," Scandinavian Journal of Gastroenterology, vol. 44, 2009, pp. 727-735.

Olsen, T., et al., "Tissue levels of tumor necrosis factor-alpha correlates with grade of inflammation in untreated ulcerative colitis," Scandinavian Journal of Gastroenterology, vol. 42, 2007, pp. 1312-1320.

Olsen, T., "TH1 and TH17 interactions in untreated inflamed mucosa of inflammatory bowel disease, and their potential to mediate the inflammation," Cytokine, vol. 56, 2011, pp. 633-640.

Olsen, T., et al. "TNF-alpha gene expression in colorectal mucosa as a predictor of remission after induction therapy with infliximab in ulcerative colitis," Cytokine, vol. 46, No. 2, 2009, pp. 222-227.

Ricciardelli, I., et al., "Anti tumor necrosis-$\alpha$ therapy increases the number of FOXP3$^+$ regulatory T cells in children affected by Crohn's disease," Immunology, vol. 125, 2008, pp. 178-183.

Rismo, R., et al., "Mucosal cytokine gene expression profiles as biomarkers of response to infliximab in ulcerative colitis," Scandinavian Journal of Gastroenterology, vol. 47, No. 5, 2012, pp. 538-547.

Rismo, R., et al. "Normalization of mucosal cytokine gene expression levels predicts long term remission after discontinuation of anti-TNF therapy in Crohn's disease," Scandinavian Journal of Gastroenterology, vol. 48, No. 3, 2013, pp. 311-319.

Rismo, R., et al. "The effect of adalimumab for induction of endoscopic healing and normalization of mucosal cytokine gene expression in Crohn's disease," Scandinavian Journal of Gastroenterology, vol. 47, No. 10, 2012, pp. 1200-1210.

Rutgeerts, P., et al., "Infliximab for Induction and Maintenance Therapy for Ulcerative Colitis," The New England Journal of Medicine, vol. 353, No. 23, 2005, pp. 2462-2476.

Sandborn, W.J., et al., "Adalimumab for maintenance treatment of Crohn's disease: results of the CLASSIC II trial," Gut, vol. 56, 2007, pp. 1232-1239.

Sands, B.E., "From Symptom to Diagnosis: Clinical Distinctions Among Various Forms of Intestinal Inflammation," Gastroenterology, vol. 126, No. 6, 2004, pp. 1518-1532.

Sands, B.E., et al., "Infliximab Maintenance Therapy for Fistulizing Crohn's Disease," The New England Journal of Medicine, vol. 350, No. 9, 2004, pp. 876-885.

Scaldaferri, F., et al., "Mucosal biomarkers in inflammatory bowel disease: key pathogenic players or disease predictors?" World Journal of Gastroenterology, vol. 16, No. 21, 2010, pp. 2616-2625.

Sutherland, L.R., et al., 5-Aminosalicyclic Acid Enemas in Treatment of Distal Ulcerative Colitis and Proctitis in Canada, Digestive Disease and Sciences, vol. 32, No. 12, 1987, pp. 64S-66S.

International Preliminary Report on Patentability and Written Opinion, dated Jun. 23, 2015, received in connection with International Patent Application PCT/GB2013/053418.

International Search Report, dated Mar. 14, 2014, received in connection with International Patent Application PCT/GB2013/053418.

BIOMARKERS IN INFLAMMATORY BOWEL DISEASE

Inflammatory bowel disease (IBD) is an immunologically mediated chronic disease. The present invention relates to identifying IBD patients with downregulated immunological pathways after treatment with high-cost biological agents. This is also based on the new concept of immunological remission-IR—which is a term that has been defined by the inventors and which is described in detail below. A determination of IR in these patients provides an indication of long term recovery, and the ability to discontinue treatment, as these patients have lower probability of relapse on discontinuation of treatment.

Inflammatory Bowel Disease is the name given to a collection of chronic inflammatory disorders that affect the gastrointestinal (GI) tract. IBD can have devastating consequences for those afflicted. In Europe alone, more than 2.2 million people have the disease, and this is increasing. In Europe and North America this has become a major health problem. Crohn's Disease (CD) and Ulcerative Colitis (UC) are the two major types of IBD, with the two conditions differing in terms of the location and the nature of the lesions present in the GI tract. The symptoms are diverse and can include abdominal pain, vomiting, diarrhoea, rectal bleeding, internal cramps, weight loss and fever, fatigue, and/or anaemia. In addition, extraintestinal manifestations such as joint, skin and eye disorders might also be present. IBD can have a serious negative impact on quality of life in view of the symptoms mentioned above, but it is rarely fatal on its own. Fatalities due to complications such as toxic megacolon, bowel perforation and surgical complications are also rare. IBD is, however, associated with an increased risk of colorectal cancer, an elevated risk of endothelial dysfunction and coronary artery disease.

No cure for IBD exists. Current treatment protocols are designed with the goal of achieving remission, as assessed by clinical and visual examination of the GI tract (e.g. by endoscopy). At this point, the patient may be switched to a lighter drug with fewer potential side effects. Every so often, an acute resurgence of the original symptoms may appear; known as a "flare-up". Treatment is likely to be required for flare-ups in most cases. The time between flare-ups may be anywhere from weeks to years, and will vary between patients.

Optimal treatment of IBD depends on the patient, the nature of the specific disease and the degree of severity. Various therapeutic strategies are available, including the use of 5-ASA (such as mesalazine), steroids (such as prednisolone), and the immunosuppressive agents azathioprine, methotrexate, 6-mercaptopurine. A combination of steroids and immunosuppresives is often used in more severe cases and an individual's treatment program will vary over time. Particularly severe cases may require surgery, such as bowel resection, strictureplasty or a temporary or permanent colostomy or ileostomy.

A relatively new treatment for IBD is anti TNFα therapy, specifically infliximab (sold as REMICADE®) and adalimumab (sold as HUMIRA), which have been used for some years in CD treatment, and more recently for the treatment of UC. This treatment is in general used for patients who have not responded to other drugs, where these drugs have caused side effects, or when surgery is not considered the right treatment. Treatment with infliximab is via infusion of the drug, over the course of several hours, requiring the patient to visit a hospital or medical centre. Current treatment protocols recommend infusion approximately every 6 to 8 weeks until visual healing of the mucosa is obtained. Treatment with adalimumab is by subcutaneous injection, once every 1 to 2 weeks.

In various studies, adalimumab and infliximab have been shown to be effective for induction of both clinical and endoscopic remission in patients with CD, as well as for maintenance of remission. It has, however, also been shown in studies of maintenance of clinical remission that a considerable proportion (50%) of patients who received placebo treatment in these studies also maintained clinical remission after one year (Sandborn W et al, Gut 2007, 56, 1232-9). As such, continued treatment with these agents may not be required for clinical remission to continue. Further, the levels of clinical benefit after infliximab treatment in UC have been shown to be variable (Rutgeerts and Sandborn, NEJM, 2005, 353:2462-76). In this study, although a high percentage (64%) of the infliximab treated group achieved clinical remission, and 42% were still in remission at the end of the follow up period, 36% of the patients in the placebo group achieved a clinical response and 20% were in clinical remission at the end of the follow up period.

Targeted biological therapy, using anti-TNF-α antibodies or similar, has therefore strongly improved the prognosis of severe IBD. This is however an extremely high cost therapy (EUR 20.000 annual expenses per patient). To be able to develop safe criteria for when to stop treatment would be very important in order to reduce the health cost and the negative side effects of long-term therapy for this group of patients. Thus, whilst this treatment provides an important improvement over previously available treatments, and has succeeded in improving the life of many patients, there are still several unresolved questions concerning the details of the management of IBD patients. One key unresolved question is when to stop treatment with anti-TNF-α. The industry recommends treating with Infliximab every 8 weeks after induction therapy. In view of the high cost of the repetitive treatment strategy, the fact that not all patients need maintenance therapy to remain in long-term remission, and the fact that following the conventional treatment regime with UC patients may lead to overtreatment, it is of great clinical interest to search for criteria to determine the optimal time to stop this treatment with anti-TNFα. A further important consideration is that the therapy can be associated with severe adverse events, such as lymphoma and serious opportunistic infections.

So far there is no general agreement as to how long the anti-TNFα therapy should be continued for, and no agreed criteria for determining the time at which treatment should be discontinued (stop criteria). According to the English NICE (National Institute of Clinic and Excellence) recommendations, treatment with this therapy after 12 months should only be continued if there is clear evidence of ongoing active disease as determined by clinical symptoms and investigation (i.e. documentation by endoscopy). It is clear that some patients who satisfy the criteria of an absence of ongoing active disease will relapse if treatment is discontinued, whereas others will only require a short treatment period to achieve long term remission. Therefore, there is a need for additional criteria with a high predictive value of a long-term remission of the disease. An agreed stop criteria for this therapy would thus significantly improve patient management.

The present inventors have shown that within the group of patients who have been treated in this way, and whose mucosa is healed according to the criteria of endoscopic remission, different clinical outcomes exist if treatment is discontinued from this point. By monitoring the disease status of patients once the treatment was discontinued, the inventors have been able to show, surprisingly, that the clinical outcomes following discontinuation of treatment can be correlated with the levels of various cytokines in the healed mucosa at the time that the treatment is stopped. In other words, although patients' mucosa may appear to be healed based on the criteria of endoscopic remission i.e. using a visual assessment, some of those patients will relapse if treatment is discontinued, whereas others will continue in remission, and it cannot be determined based on this endoscopic assessment alone, or on the basis of any known criteria for evaluating IBD, which group a patient is likely to fall into. This can, however, be determined by measuring the levels of cytokines in the GI mucosa, as is described in more detail below.

There are two general approaches to evaluating patients with IBD. The first involves the visual examination of the mucosa and relies on the observation of signs of damage to the mucosa, in view of the fact that IBD is manifested by the appearance of inflammation and ulcers in the GI tract. Any procedure that allows an assessment of the mucosa can be used. Examples include barium enemas, x-rays, and endoscopy. An endoscopy may be of the oesophagus, stomach and duodenum (esophagogastroduodenoscopy), small intestine (enteroscopy), or large intestine/colon (colonoscopy, sigmoidoscopy). These techniques are used to identify areas of inflammation, ulcers and abnormal growths such as polyps.

Scoring systems based on this visual examination of the GI tract exist to determine the status and severity of IBD, and these scoring systems are intended to ensure that uniform assessment of different patients occurs, despite the fact that patients may be assessed by different medical professionals, in diagnosis and monitoring of these diseases as well as in clinical research evaluations. Examples of evaluations based on visual examination of UC are discussed and compared in Daperno M et al (J Crohns Colitis. 2011 5(5): 484-98).

Clinical scoring systems also exist, with the same purpose. The findings on endoscopy or other examination of the mucosa can be incorporated into these clinical scoring systems, but these scoring systems also incorporate data based on symptoms such as stool frequency, rectal bleeding and physician's global assessment. IBD has a variety of symptoms that affect quality of life, so certain of these scoring systems also take into account a quantitative assessment of the effect on quality of life as well as the quantification of symptoms.

One example of a scoring system for UC is the Mayo scoring system (Schroeder K W et al N Eng J Med 1987, 317(26):1625-1629), but others exist such as the UCDAI scoring system (Sutherland L R et Gastroenterology 1987, 92:1894-8) and examples of evaluations based on these and other scoring systems for UC are discussed and compared in Cooney et al supra).

An example of a scoring system for CD is the Crohn's Disease Activity Index (CDAI) (Sands B et al 2004, N Engl J Med 350 (9): 876-85); most major studies use the CDAI in order to define response or remission of disease. The Harvey-Bradshaw index is a simpler version of the CDAI which consists of only clinical parameters (Harvey, R et al 1980 Lancet 1 (8167): 514). The impact on quality of life is also addressed by the Inflammatory Bowel Disease Questionnaire (IBDQ) (Irvine E, et al 1994, Gastroenterology 106 (2): 287-96).

The above criteria are useful for diagnosing and monitoring IBD and were newly assessed in the Scientific Workshop of the ECCO II (European Crohn's and Colitis Organization).: Measures and markers of prediction to achieve, detect, and monitor intestinal healing in inflammatory bowel disease. (Daperno et al, J Crohns Colitis. 2011; 5(5):484-98). However, it is clear that there is a need for improved criteria for determining the success or otherwise of anti-TNFα treatment, and determining whether and when to discontinue treatment. Endoscopy is time consuming and invasive. It is furthermore clear that the existing methods of assessing IBD are simply not refined enough to enable an informed decision to be made about whether a patient may discontinue with treatment. This is clear because within the group of patients who have achieved endoscopic remission (or even completely visually healed mucosa) following a period of treatment, patient subgroups exist, with different prospects for continued remission if treatment is then discontinued from that point. These subgroups are believed to reflect different degrees of healing of the GI mucosa, which cannot be detected by current diagnostic means.

The term Immunological Remission (IR), as adopted herein, is used to define those patients who are more likely to continue in long term recovery or remission and have a reduced likelihood of relapse if treatment is discontinued. For the purposes of the present invention and in view of the data presented herein, a patient is classified as being in IR if at least one of the cytokines discussed in more detail herein is at a normalised level, and a finding that a patient is in IR can be made on the basis of determining the level of one of these cytokines. As discussed in more detail below, there may be patients in which all intestinal inflammatory pathways mediating IBD are down-regulated to normalization following treatment. In preferred embodiments, a patient is classified as being in IR if two (or at least two), or three (or at least three) of the cytokines discussed in more detail herein are at a normalised level, and a finding that a patient is in IR can be made on the basis of determining the level of two (or at least two), or three (or at least three) of these cytokines.

A patient who has achieved endoscopic remission (e.g. has visually healed mucosa) following a period of treatment and who is in IR is more likely to continue in long term recovery or remission and have a reduced likelihood of relapse if treatment is discontinued. IR is thus associated with long term recovery or remission and a reduced risk of relapse, without continued treatment, i.e. patients who are in IR are more likely to continue to remain in clinical remission than those who are not. These patients are thus more likely to be able to discontinue further treatment without subsequent relapse, thus saving valuable medical resources and with the personal benefit of reducing or avoiding the risk of side effects associated with the continued treatment as well as the inconvenience undergoing regular treatment, which may require a visit to a medical centre. Because the patients are in IR and they have a reduced risk of relapse without further treatment, an informed decision can be made about discontinuing with the treatment, Other patients may have achieved endoscopic remission (e.g. have a visually healed mucosa) but have not achieved IR. These patients appear to have recovered on the basis of the existing clinical assessments, but as they are not in IR, they are less likely to achieve long term recovery without further treatment, and more likely to relapse, compared to those patients who are in IR. IR is thus associated with long term recovery and continued remission from symptoms of IBD following treatment with anti TNFα treatment, and without further anti TNFα treatment.

The inventors have found that where an apparently healed mucosa is associated with increased immunological activity as compared to healthy subjects, the chance of relapse is greater (than when immunological activity is not increased) and thus the patient is not in IR. 'Immunological activity' in this context refers to cytokine levels, in particular levels of TNFα, IL-17 and IFN-γ.

Thus whilst endoscopic remission and mucosal healing in IBD is associated with lower rates of abdominal surgery and hospitalization and also with longer relapse-free survival during ongoing anti-TNFα therapy, and documentation of mucosal healing by endoscopy has become a critical component of outcome measurement, present methods do not enable the identification of this newly identified patient subgroup or a determination of whether an individual is in this particular patient subgroup. The identification by the inventors of this patient subgroup, and the associated methods provided by the invention that enable this subgroup to be identified readily represents a significant advance.

Biomarkers are used in many conditions for diagnosis and monitoring of disease states, but there are, however, still limitations in the utility and clinical relevance of mucosal markers, and despite research in this area to date, the data has been insufficient to make recommendations on when to stop this therapy in patients with IBD.

As well as identifying the existence and clinical relevance of this subgroup of patients, the inventors have established a way of identifying patients who are in this subgroup. They have shown that the presence of IR in IBD can be determined on the basis of the levels of certain cytokines in the GI mucosa, selected from TNFα, IL-17 and IFN-γ. As such, determining the levels of expression of one or more of these cytokines in GI mucosa taken from patients who have been treated with anti-TNFα therapy and who might for example have achieved endoscopic remission (e.g. a visually healed mucosa) will allow a determination of whether a patient is in IR. Specifically, the inventors have shown that in IBD patients who have been treated with anti-TNFα therapy and who have achieved endoscopic remission (e.g. visually healed mucosa), the levels of certain cytokines in the GI mucosa could be used to predict relapse of disease after discontinuation of treatment.

The inventors measured cytokine levels in mucosal biopsies taken from IBD patients who had achieved endoscopic remission alone or endoscopic and clinical remission (assessed by standard clinical criteria). The cytokine levels in the mucosal biopsies from the treated patients were compared to the cytokine levels in mucosal samples taken from control individuals. The patients were followed after discontinuation of therapy until relapse, and the time to relapse was assessed. The inventors found that a significant proportion of patients were still in remission after 52 weeks (21% of 50 evaluated UC patients and 26% of 27 evaluated CD patients). Importantly, a much higher proportion of patients with normalised levels of TNFα, IFNγ and/or IL-17 were still in remission after 52 weeks. Expression levels of these three cytokines in mucosa from patients in endoscopic remission (e.g. with visually healed mucosa) were furthermore significantly higher in patients who relapsed before 26 weeks than in those who did not relapse and were also significantly higher in patients who relapsed before week 52 versus non-relapsers. In contrast, elevated levels of cytokine gene expression in mucosa from patients in endoscopic remission (e.g. with visually healed mucosa) increased the risk of relapse.

It is clear from the above that patients who have normalised levels of one or more of these cytokines (i.e. who are in IR) are less likely to relapse following discontinuation of anti TNFα treatment than those that are not in IR and these patients are more likely to be in long term recovery or remission than those that are not in IR. In other words there is a strong correlation between the levels of one or more of these cytokines in the mucosa and the presence of IR. This allows a determination be made about whether a patient is in IR on the basis of an assessment of the levels of these cytokines in the GI mucosa. This in turn allows a decision to be made concerning the management of the treatment of the patient. It is of interest to more precisely select the patients who need to continue with the anti-TNFα medication, both for optimal treatment strategy for the individual patient and for optimal cost-benefit strategy for the hospital.

Thus in a first embodiment the invention provides a method of determining whether a patient with inflammatory bowel disease (IBD) and who has been treated with anti TNFα therapy is in immunological remission (IR), said method comprising determining the level of a cytokine selected from TNFα, IL-17 and IFN-γ in a GI mucosal sample from said patient.

The method may optionally comprise comparing the level of cytokine selected from TNFα, IL-17 and/or IFN-γ in said sample to a control level. It should be noted however that although the control level for comparison would generally be derived by testing an appropriate control or a set of control subjects, the methods of the invention would not necessarily involve carrying out active tests on such a control or a set of control subjects but would generally involve a comparison with a control level which had been determined previously from a control subject or from a set of control subjects.

An increased level of a cytokine selected from TNFα, IL-17 and IFN-γ in said sample is indicative of the absence of IR in said patient. A normalised level of cytokine selected from TNFα, IL-17 and IFN-γ in said sample is indicative of the presence of IR in said patient. This is illustrated in the FIGS. 1-4. "Increased" and "normalised" levels are generally related to control values.

Preferably the level of the cytokine in question is determined by analysing a test sample which is obtained from or removed from said patient by an appropriate means. The determination is thus preferably carried out in vitro.

For an identification of IR to be made, the level of the relevant cytokine in the test sample or subject must be "normalised", i.e. reduced to around the levels that are seen in control subjects (e.g. healthy patients, as discussed in more detail below). The cytokine level may not return to these normalised levels until some time after endoscopic remission (alone or with clinical remission, as assessed by current evaluation protocols) is attained. In other words continued treatment may be required in order to achieve the state of IR, even if the patient's disease status, as assessed by current means, would be considered to be remission (endoscopic remission alone or endoscopic and clinical remission).

In order to determine what level of cytokine corresponds to a "normalised" level it is thus necessary to refer to levels of the relevant cytokine that are observed in one or more controls. At its broadest "normalised" means a level which does not exceed or significantly exceed the level of the relevant cytokine that is observed in controls.

This can be expressed in relative or absolute terms. In relative terms the cytokine level is "normalised" when it is below a predetermined cut-off value, when compared to the control level. A patient is considered to have a normalised level of cytokine if the level of cytokine falls below the cut-off value. For example, at its simplest, if the assessment is to be made based on a comparison with a control level, a normalised level may be up to 200% (preferably 195, 190, 185, 180, 175, 170, 165, 160, 155, 150, 145, 140, 135, 130, 125, 120, 115, 110, 105, 104, 103, 102, 101) of the control level. In other words the cut-off for normalisation can be defined as 200% (preferably 195, 190, 185, 180, 175, 170, 165, 160, 155, 150, 145, 140, 135, 130, 125, 120, 115, 110, 105, 104, 103, 102, 101) of the control level, i.e. a patient is considered to have a normalised level of cytokine if the level of cytokine falls below 200% (preferably 195, 190, 185, 180, 175, 170, 165, 160, 155, 150, 145, 140, 135, 130, 125, 120, 115, 110, 105, 104, 103, 102, 101) of the control.

As discussed in more detail below, the control level can be the level of that cytokine in a single control sample or the average (e.g. the mean) level from multiple control samples.

When the range of what is considered to be "normalised" is determined based on multiple control samples, the level of cytokines in these multiple control samples can be used to define the cut-off for normalisation. For example a cut-off for normalisation of cytokine expression in IBD patients can be defined by the upper bound of 3, 2.5, 2.4, 2.3, 2.2, 2.1, 2, 1.9, 1.8, 1.7, 1.6, 1.5 or 1 standard deviations from the mean cytokine level in the control samples (or up to these amounts). The mean and standard deviation are determined by standard statistical analysis.

A determination can alternatively be made based on absolute levels of the cytokines, as is set out in more detail below. The cut off for normalisation for each cytokine are as follows.

For UC, a range of up to 10000 copies (e.g. up to 9000, 8000, 7000, 6000, 5000 or 5000-15000, 6000-14000, 7000-13000, 8000-12000, 9000-11000 copies TNFα/µg total RNA may be considered to be "normalised". For CD, a range of up to 10000 copies (e.g. up to 9000, 8000, 7000, 6000, 5000 or 5000-15000, 6000-14000, 7000-13000, 8000-12000, 9000-11000 copies) TNFα/µg total RNA TNFα may be considered to be "normalised". These values thus may provide the cut off level for normalisation for this cytokine for each condition.

As discussed above, the presently used clinical criteria for assessing the status of IBD patients after anti TNFα therapy are unsatisfactory. There are recognised systems for assessing remission in IBD, many of which are based on a visual examination of the mucosa. As discussed in more detail elsewhere, full healing of the mucosa (e.g. a visually normal mucosa or a mucosa with only inactive disease), or the presence only of mild indications of disease (e.g. in line with the presence of mild erythema, decreased vascular pattern and/or mild friability) is considered to be an indication of endoscopic remission. When the GI mucosa of patients who have been treated with anti TNFα is examined, the status of the mucosa can be determined but it is clear that the presently used clinical criteria alone do not allow a satisfactory distinction to be made, within the group of patients who are considered to be in endoscopic remission, between those who are likely to relapse if treatment is discontinued and those who are not. It is clear from the inventors' work that of the patients who are in endoscopic remission, some are more likely to relapse if treatment is discontinued than others.

The findings of the inventors have thus allowed a new subgroup of IBD patients to be identified within those patients in endoscopic remission following anti-TNFα treatment, those who are in IR. IR is associated with a reduced risk of relapse if treatment is discontinued and with long term recovery or remission, and also with a particular profile of mucosal gene expression, particularly the cytokines IL-17, TNFα and IFNγ i.e. reduced immunological activity.

The inventors' identification of this subgroup and the characterisation of the subgroup on the basis of the mucosal gene expression profile thus allows it to be determined on the basis of the expression levels of one or more of these cytokines whether a patient is in IR.

IBD has an immunological component and by identifying, as the inventors have done, appropriate markers of this, the status of the disease can be measured more accurately than current methods allow. An IBD patient in IR is thus characterised by normalised levels of cytokine selected from IL-17, TNFα and IFNγ in the GI mucosa.

The cytokines referred to in the methods of the invention have been shown by the inventors to be elevated in the GI mucosa of patients who, despite being in endoscopic (and optionally also clinical) remission, are more likely to relapse if treatment is discontinued, compared to those who do not have these elevated levels of cytokines.

The inventors determined the levels of cytokines in the GI mucosa of IBD patients who had been treated with TNFα and who had achieved endoscopic remission and followed those patients after treatment was stopped.

For patients with CD, all patients with normalised TNFα mRNA expression and 88% of evaluated patients with normalized IL-17 mRNA expression were still in remission at week 26, whereas without normalization of TNFα and IL-17, only 24% and 35% of patients, respectively, were still in remission at this time-point (Example 1). After 52 weeks, 63% and 67% of evaluated patients with normalized TNFα and IL-17 gene expression levels, respectively, were still in remission. Without normalized TNFα and IL-17 mRNA expression levels, only 11% and 14% of evaluated patients, respectively, were still in remission at 52 weeks. With univariate Cox analysis lack of normalisation of IL-17 and TNFα was significantly associated with relapse. Therefore for CD patients in the methods of the invention, the cytokines are preferably selected from IL-17 and TNFα, even more preferably TNFα.

For patients with UC, Cox-regression analysis demonstrated that higher levels of TNFα and IFN-γ expression were significantly associated with relapses within 18 months (HR=2.2, p=0.04, HR=2.5, p=0.03, respectively) and normalization of IL-17 tended to predict long-term remission. As such, for UC patients in the methods of the invention the cytokines are preferably selected from IFNγ and TNFα, even more preferably TNFα.

The amino acid and nucleic acid sequences of these cytokines are all known and are available in the art. As such, the skilled person may readily determine an appropriate method to determine the level of the relevant cytokine.

In most cases it is sufficient for the level of one cytokine to be detected but the methods of the invention may involve the detection of the level of two or all three of the cytokines as referred to herein (e.g. at least 1, at least 2 or at least 3 of the cytokines as referred to herein). For example, the methods of the invention may involve determining the level of IL-17, TNFα or IFNγ. Alternatively the methods may involve determining the level of IL-17 and TNFα, or determining the level of IL-17 and IFNγ, or determining the level TNFα and IFNγ, or determining the level of IL-17, TNFα and IFNγ. Measurement of the level of TNFα is especially preferred, IL-17 is an excellent alternative and both may be measured together in some preferred embodiments of the invention.

For patients with CD, the methods of the invention may preferably involve determining the level of IL-17, TNFα or IFNγ, or IL-17 and TNFα. For patients with UC the methods of the invention may preferably involve determining the level of IL-17, TNFα or IFNγ, or IFNγ and TNFα.

As discussed above, once the level of the relevant cytokine has been determined, it is then determined whether said level is normalised or elevated in order to determine whether said patient is in IR.

The levels of the cytokines referred to above may be determined alone or in the combinations referred to above. The levels of the cytokines referred to above may also be determined in combination with other biomarkers, which could be further cytokines or other molecules. There are many other potential biomarkers as described in a recent review (Florholmen J & Fries W, Scand J Gastroenterol 2011. 2011, 46, 1407-17), but so far not tested. If other biomarkers are tested for, the level of said biomarker may be determined or it may merely be the presence or absence of that biomarker that is ascertained.

As mentioned above a finding of IR may be made on the basis of at least 1 (or at least 2 or at least 3) cytokine being normalised (e.g. detecting at least 1 cytokine (or at least 2 or at least 3)). A patient in IR can thus be further classified according to the number of cytokines that are normalised in the GI mucosa of that patient. Patients with a higher number of normalised cytokines in the GI mucosa have a better prognosis.

If the method involves the determination of the level of more than one cytokine or biomarker, the method may be performed on a single sample in parallel (e.g. by multiplex analysis) or on a single sample in sequence (e.g. where the single sample is assayed multiple times, once for each biomarker or cytokine that is to be detected or the level thereof determined). Alternatively, the analysis may be performed on multiple (e.g. 2, 3, 4, 5, 6, 7, 8 or at least 2, 3, 4, 5, 6, 7, or 8) samples obtained from the same patient.

Patients who are in IR have a reduced likelihood of relapse compared to those who are not in IR. Relapse in this context means a recurrence of the symptoms of IBD. The symptoms experienced by the individual patient are diverse but the common feature is the presence of lesions in the GI tract and, in view of this, relapse is characterised by a return of such lesions and/or an assessment based on one of the clinical scoring systems discussed herein. As such, relapse is said to have occurred if said patient is no longer in clinical remission and/or endoscopic remission as defined by one or more of these tests. Preferably relapse is defined for UC patients as being a UCDAI score of >3 and/or endoscopic score of >1 according to this test or a Mayo score with the same levels as UCDAI score. For CD patients relapse is preferably defined as being a CDAI increase of >70 points and/or endoscopic relapse, which could be for example a return of characteristic lesions in the GI tract, or a finding that the patient is no longer in endoscopic remission as defined herein (e.g. the appearance of redness and/or ulcerations). A reduced risk of relapse thus means that in any defined period (e.g. a period of at least or up to 0.5, 1, 1.5, 2, 3, 4, 5, 6, 7, 8, 9 or 10 years), a patient with IR is less likely to relapse than a patient who is not in IR. Conversely, a patient who is in IR has an increased likelihood of long term recovery which is defined by an absence of relapse.

The methods of the invention as described herein can be carried out on any subject which may suffer from IBD. The methods are generally carried out on mammals, for example humans, other primates (e.g. monkeys), laboratory mammals (e.g. mice, rats, rabbits, guinea pigs), livestock mammals (e.g. horses, cattle, sheep, pigs) or domestic pets (e.g. cats, dogs). In preferred embodiments the mammals are humans. However, in other embodiments, the cytokines can be used as IR markers in any appropriate animal model.

The patient has IBD, which is the name given to a collection of chronic inflammatory disorders affecting the GI tract. The patient preferably has CD or UC.

The invention relates to identifying the status of IR in patients who have been treated with anti TNFα therapy. By anti TNFα therapy it is meant any therapy that inhibits or antagonises TNFα. This could include inhibiting the production of TNFα or its receptor, e.g. by inhibiting its transcription or translation, or inhibiting its activity, directly or indirectly. Various methods for achieving this are known in the art. Inhibitors and antagonists or TNFα thus include antisense molecules, RNAi molecules, ribozymes, antibodies (e.g. a monoclonal antibody) or other binding proteins and small molecules. Any of these may be directed against TNFα or its receptor.

Examples of monoclonal antibodies include infliximab (REMICADE®), adalimumab (HUMIRA®), certolizumab pegol (CIMZIA®), and golimumab (SIMPONI®). Example of another binding molecule is etanercept (ENBREL®), which is a circulating receptor fusion protein. Examples of small molecules are xanthine derivatives (e.g. pentoxifylline) and Bupropion (the active ingredient in the smoking cessation aid Zyban and the antidepressant Wellbutrin). Several 5-HT2A agonist hallucinogens including (R)-DOI (2,5-Dimethoxy-4-iodoamphetamine), TCB-2 (1-[(7R)-3-bromo-2,5-dimethoxybicyclo[4.2.0]octa-1,3,5-trien-7-yl]methanamine), LSD (Lysergic acid diethylamide) and LA-SS-Az (Lysergic acid 2,4-dimethylazetidide) have unexpectedly also been found to act as potent inhibitors of the TNFα receptor.

The anti TNFα treatment is preferably a binding molecule which binds to TNFα or its receptor, but preferably to TNFα. More preferably the treatment is a monoclonal antibody, particularly infliximab (REMICADE®) (95% humanized) or the fully humanized adalimumab (HUMIRA®).

Patients will have been subjected to anti TNFα treatment. The treatment has preferably been carried out for a period of time that results in clinical remission alone or clinical and endoscopic remission as defined herein. In general the treatment is administered periodically; the administration dose and frequency will depend on the specific treatment that is used. For example, infliximab is routinely administered at a dose of 5 mg/kg by periodic infusion e.g. every 2-8, 3-7 or 4-6 weeks for a period of at least 3 months. Adalimumab is routinely given with an initial dose of 80 mg followed by 40 mg at approximately 2 week intervals for at least 12 weeks.

Thus the patient has preferably been treated with an anti TNFα therapy over a period of at least 2, 3, 4, 5 or 6 months.

The methods of the invention are advantageous since they allow a more accurate picture of the healing status of the mucosa to be obtained than present methods, hence allowing predictions to be made about the future progress of the disease and whether a patient can discontinue treatment. The methods of the invention are particularly useful where a finding of endoscopic remission (and optionally also clinical remission) has been made. The method of the invention is able to distinguish, within that patient group, the subgroup of patients who are in IR. The patient is thus preferably a patient in endoscopic remission (and further preferably also in clinical remission), both of which are defined in more detail below.

There are various ways to assess IBD patients. Assessments can be made on the basis of endoscopic assessment;

the clinical scoring systems such as the Mayo index and the UCDAI system for UC and the CDAI for CD can use this endoscopic assessment as part of the overall scoring system, alternatively only the non-invasive components can be used (e.g. stool frequency and rectal bleeding).

Table 1 below shows the components of the Sutherland Index, also known as the ulcerative colitis disease activity index (UCDAI). UCDAI score according to D'Haens G et al, (Gastroenterology 2007; 132: 763-86) which is a modified version of the initial Mayo score (Schroeder K W et al. N Eng J Med 1987, 317, 1625-29) but has the same components and same score system.

Stool frequency

0 = Normal
1 = 1-2 stools/day > normal
2 = 3-4 stools/day > normal
3 = >4 stools/day > normal Rectal bleeding 0 = None
1 = Streaks of blood
2 = Obvious blood
3 = Mostly blood Mucosal appearance 0 = Normal
1 = Mild friability
2 = Moderate friability
3 = Exudation, spontaneous hemorrhage Physician's rating of disease activity 0 = Normal
1 = Mild
2 = Moderate
3 = Severe The UCDAI score ranges from 0 to 12 with a higher score indicating more severe disease.

Table 2 shows the components of the Mayo scoring system

| Components of the Mayo Score | |
|---|---|
| Stool frequency | |
| 0 | Normal |
| 1 | 1-2 stools/day more than normal |
| 2 | 3-4 stools/day more than normal |
| 3 | 5 or more stools/day more than normal |
| Rectal bleeding | |
| 0 | None |
| 1 | Visible blood with stool less than half the time |
| 2 | Visible blood with stool half of the time or more |
| 3 | Passing blood alone |
| Mucosal appearance at endoscopy | |
| 0 | Normal or inactive disease |
| 1 | Mild disease (erythema, decreased vascular pattern, mild friability) |
| 2 | Moderate disease (marked erythema, absent vascular pattern, friability, erosions) |
| 3 | Severe disease (spontaneous bleeding, ulceration) |
| Physician rating of disease activity | |
| 0 | Normal |
| 1 | Mild |
| 2 | Moderate |
| 3 | Severe |

Thus the Mayo score ranges from 0 to 12 with a higher score indicating more severe disease. If the non invasive components only are used, the Mayo score ranges from 0 to 6.

For UC patients, clinical remission is defined as a score of 2 points or lower using the full Mayo score, with no individual subscore exceeding 1 point, and endoscopic remission is defined as a score of 0 or 1 based on the endoscopic component of this score. Using the UCDAI score clinical remission is in general defined as a score of 3 points or lower, and endoscopic remission is defined as a score of 0 or 1 based on the endoscopic component of this score. A more preferred definition of endoscopic remission for UC patients is a score of 0 in the endoscopic component of the UCDAI or mayo scoring system.

Table 3 shows the CDAI (Best et al 1976 Gastroenterology 70 (3): 439-444). The index consists of eight factors, each summed after adjustment with a weighting factor.

| Clinical or laboratory variable | Weighting factor |
|---|---|
| Number of liquid or soft stools each day for seven days | ×2 |
| Abdominal pain (graded from 0-3 on severity) each day for seven days | ×5 |
| General well being, subjectively assessed from 0 (well) to 4 (terrible) each day for seven days | ×7 |
| Presence of complications* | ×20 |
| Taking Lomotil or opiates for diarrhea | ×30 |
| Presence of an abdominal mass (0 as none, 2 as questionable, 5 as definite) | ×10 |
| Hematocrit of <0.47 in mrn snf <0.42 in women | ×6 |
| Percentage deviation from standard weight | ×1 |

*One point each is added for each set of complications: the presence of joint pains (arthralgia) or frank arthritis; inflammation of the iris or uveitis; presence of erythema nodosum, pyoderma gangrenosum, or aphthous ulcers; anal fissures, fistulae or abscesses; other fistulae; fever during the previous week.

Clinical remission of Crohn's disease is defined as a score in the CDAI of less than 150, severe disease being defined as a value of greater than 450. Endoscopic analysis does not form part of the CDAI but is a further useful tool for evaluating remission.

In general, there is no general agreement of how to grade the endoscopic inflammation of CD but the most used is the SES-CD (Daperno M, et al. Gastrointest Endosc 2004; 60 (4): 505-512). Moreover, there is also no universal agreement of the definition of endoscopic remission. In Example 1 in which CD patients are analysed a finding of endoscopic remission is based on no ulceration or redness (inflammation).

In the present application, for CD patients, endoscopic remission is defined as the presence only of mild indications of disease (e.g. in line with the presence of mild erythema, decreased vascular pattern and/or mild friability), or more preferably full healing of the mucosa (e.g. a visually normal mucosa or a mucosa with only inactive disease, e.g. the absence of any (i.e. no) ulceration or redness (inflammation)).

Patients to be assessed in accordance with the methods of the invention have been treated with an anti TNFα treatment as defined above and preferably are in endoscopic remission alone or endoscopic and clinical remission.

Where the patient is a UC patient, the patient preferably has an endoscopic sub-score of 0 or 1 (preferably 0) in the UCDAI test and optionally also an overall UCDAI score of less than 3 (preferably less than 2 or less than 1). Alternatively the UC patient may have an endoscopic sub-score of 0 or 1 (preferably 0) in the Mayo index and optionally also an overall score in this test of less than 2 (preferably less than 1), preferably with no individual sub-score exceeding 1 point.

Where the patient is a CD patient, the patient has a CDAI score of less than 150, (preferably less than 120 or less than 100) and/or endoscopic remission as defined above (preferably no redness and/or ulceration by endoscopy)

In all cases the patient preferably has a fully healed GI mucosa, i.e. a GI mucosa which appears visually normal with no sign of active disease.

The methods of the invention thus optionally comprise the additional step of carrying out an endoscopic evaluation alone or with a clinical evaluation of the patient, e.g. in order to determine whether said patient is in endoscopic remission and/or clinical remission as defined herein.

As noted above, there are other scoring systems for the evaluation of these diseases and these may be used to assess endoscopic and/or clinical remission and the patient need not have been assessed using one of the systems referred to above.

The invention also further provides a method of obtaining information relevant to a diagnosis of IR in a patient with inflammatory bowel disease (IBD) and who has been treated with anti TNFα therapy, said method comprising determining the level of a cytokine selected from TNFα, IL-17 and IFN-γ in a GI mucosal sample from said patient. Preferred aspects of this method are as disclosed elsewhere herein.

In such a method information about the level of cytokine is used together with one or more other clinical or laboratory investigations in order to provide information about the IR status of a patient. Examples of such other clinical or laboratory investigations include visual examination of the GI tract and clinical assessment using the IBD scoring systems discussed elsewhere herein.

The invention also further provides a method for the prognosis of a patient with inflammatory bowel disease (IBD) and who has been treated with anti TNFα therapy, said method comprising determining the level of a cytokine selected from TNFα, IL-17 and IFN-γ in a GI mucosal sample from said patient. The level of cytokine is indicative of the prognosis for that patient, with an increased cytokine level being indicative of a prognosis that the patient is more likely to relapse and/or less likely to continue in remission without continued treatment and/or a normalised level being indicative of a prognosis that the patient is less likely to relapse and/or more likely to continue in remission without continued treatment. Preferred aspects of this method are as disclosed elsewhere herein.

For this prognostic use it is assumed that there is an association between (1) risk of relapse and/or absence of risk of continuing in remission without further treatment and (2) cytokine levels, with "low risk" patients (those who are less likely to relapse and/or more likely to continue in remission) having levels close to the cutoff limit, but with any increasing level associated with worsening of prognosis. In general the higher the level of cytokine, the worse the prognosis.

The term "prognosis" as used herein includes a risk prediction of the probable course and clinical outcome associated with a disease. Associated with this is also the ability to classify or discriminate patients according to the probability of whether various treatment options may be of benefit to an individual. In the present case, said prediction of clinical outcome includes a prediction of any relapse without continued anti TNFα treatment and hence the need or benefit to the patient of continued anti TNFα treatment.

The methods of the invention can also be used to identify subjects requiring more intensive monitoring or subjects which might benefit from therapeutic intervention (e.g. continued anti TNFα treatment).

Thus, in a yet further aspect, the present invention provides a method to identify within a group of patients with inflammatory bowel disease (IBD) and who have been treated with anti TNFα therapy those patients who require more intensive or continued monitoring or who require therapeutic intervention (e.g. continued anti TNFα treatment), said method comprising determining the level of a cytokine selected from TNFα, IL-17 and IFN-γ in a GI mucosal sample from said patient. In other words, the methods of the invention can be used to identify at risk patients who should be monitored more closely than those for whom treatment is considered successful and complete and/or require further therapeutic intervention to treat their IBD. This method of categorising patients is especially useful for a patient or patient population who are in endoscopic remission.

Conversely, the methods can identify patients requiring less intensive monitoring or patients who do not require further therapeutic intervention (e.g. continued anti TNFα treatment). Preferred aspects of this method are as disclosed elsewhere herein.

The methods of the invention can also be used to monitor the progress of disease in a subject. The methods of the present invention can thus be used to monitor the progress of IBD, to assess the effectiveness of therapy (e.g. anti TNFα therapy) or to monitor the progress of therapy, i.e. can be used for active monitoring of therapy. In such cases serial (periodic) measurement of levels of the cytokines, for a change in said levels will allow the assessment of whether or not, or the extent to which, therapy has been effective and/or whether or not a relapse might be occurring. Preferred aspects of this method are as disclosed elsewhere herein.

A decrease in the level of the cytokine or maintenance of normalised levels is indicative of improvement or long term remission.

As discussed herein there is a significant clinical and economic benefit to ceasing anti TNFα therapy at the appropriate time. The present invention solves this problem and thus, alternatively viewed, the present invention provides a method of determining whether anti TNFα therapy can be discontinued in a patient suffering from IBD, said method comprising determining the level of a cytokine selected from TNFα, IL-17 and IFN-γ in a GI mucosal sample from said patient.

Preferred embodiments, features and additional steps described above in the context of other methods of the invention apply, mutatis mutandis, to this method and, indeed, to all methods or kits of the invention. In particular, once the cytokine level has been determined it is preferably compared to a control level. This comparison allows a determination to be made about whether the cytokine level in the patient has normalised (or normalised to such an extent) so that anti TNFα therapy can be discontinued. If the cytokine level is determined to be elevated then the clinical decision would usually be to continue anti TNFα therapy. If the cytokine level is determined to be normalised then the clinical decision would usually be to discontinue anti TNFα therapy. A control level may, in all methods, be a reference value or a level determined from one or more other samples, e.g. of a healthy subject or an earlier sample from the patient in question. The method may further include the step of discontinuing or continuing said treatment.

As noted above, the invention has particular utility in terms of determining whether a patient can discontinue treatment with anti TNFα. A patient who is in IR is less likely to require continued treatment to remain relapse free, or to remain in continued remission than a patient who is not in IR. As such, if a determination is made that a patient is in IR, treatment with anti TNFα may be discontinued. If a determination is made that a patient is not in IR, continued treatment with anti TNFα may be beneficial.

Thus in a further aspect, the method of determining whether a patient with inflammatory bowel disease (IBD) and who has been treated with anti TNFα therapy is in immunological remission (IR), as defined herein, further includes the step of discontinuing said treatment with anti TNFα if said patient is in IR or continuing said treatment with anti TNFα if said patient is not in IR.

If treatment is continued then the method may be repeated at regular intervals as discussed above in connection with monitoring, such that at each time point a decision is made (and optionally acted upon) about whether to continue or discontinue treatment with anti TNFα. This has particular application if the initial time that the method is carried out it is found that the patient is not in IR; treatment can then be continued until such a time as it is found that the patient is in IR. The method may also be carried out on a patient who has previously been treated with anti TNFα but who has stopped the treatment (e.g. but not limited to, as a result of an initial finding that he or she is in IR). If the methods are repeated, this could be at e.g. 6, 12, 18, 24, 36, 48 month intervals, or at intervals of at least these amounts.

Preferably the assessment of cytokine levels is only carried out on a patient in endoscopic remission (e.g. having visually healed mucosa) and all methods referred to above thus further optionally comprises the step of carrying out an endoscopic assessment of said patient before assessing cytokine levels.

The invention also provides an assay method comprising
(i) obtaining a GI mucosal sample from a patient with IBD and who has been treated with anti TNFα therapy;
(ii) optionally processing said sample;
(iii) measuring the level of a cytokine selected from TNFα, IL-17 and IFN-γ in said sample;
(iv) comparing the level measured in step (iii) with a control level, wherein an increased cytokine level identifies the patient as not being in IR, whereas a normalised cytokine level identifies the patient as in IR.

This method may conveniently be used in order to decide whether or not to stop treatment of the patient, in particular whether to stop anti TNFα treatment. The method provides an improved stop-criteria.

Alternatively stated the invention provides a method of treating IBD in a patient said method comprising:
(i) administering an anti TNFα treatment to said patient, and
(ii) determining whether said patient is in IR,
wherein if said patient is in IR, anti TNFα treatment is discontinued and if said patient is not in IR, anti TNFα treatment is continued.

The step of determining whether said patient is in IR is preferably carried out in accordance with the methods described elsewhere herein. Preferably step (ii) is only carried out on a patient in endoscopic remission as defined herein and said method further optionally additionally comprises the step of carrying out an endoscopic assessment of said patient before step (ii).

The GI tract contains mucous membranes (mucosa). These are the linings of the GI tract and they are of mostly endodermal origin, and covered in epithelium. The mucosa thus contains epithelium, the laminum propria and the muscularis mucosa. The samples of use in the invention are mucosal samples. Such tissue samples may be obtained by biopsy e.g. during an endoscopic procedure, or may be obtained from part of a GI tract tissue which has been removed surgically and may be a portion of the excised tissue. Preferably the sample is obtained from the lower GI tract, i.e. from the jejunum, the ileum, the cecum, the colon, the rectum or the anus.

The methods of the invention may thus optionally further comprise the step of obtaining the sample from the patient, e.g. the step of obtaining a sample of GI mucosa from the patient.

The sample may be used in the methods of the invention in the form in which it was initially retrieved. The sample may also have undergone some degree of manipulation, refinement or purification before being used in the methods of the invention. Thus the term "sample" also includes preparations thereof, e.g. relatively pure or partially purified starting materials, such as semi-pure preparations of the above mentioned samples. The term "sample" also includes preparations of the above mentioned samples in which the RNA of the sample, has undergone reverse transcription.

The way in which the sample is manipulated, refined or purified will depend on the form in which the cytokine is to be detected. The purification may be slight, for instance amounting to no more than the concentration of the tissue, solids, or cells of the sample into a smaller volume or the separation of cells from some or all of the remainder of the sample. Representative cell isolation techniques and tissue manipulation, refinement or purification are described in the art.

The sample may be manipulated to enable the components of the detection method to access the material to be detected. For example the contents of individual cells in the sample may be released from the cells, e.g. by homogenisation or by lysing the cells of the sample, or by making tissue sections. The material to be detected e.g. mRNA or cDNA or protein may furthermore be fully or partially purified therefrom using standard methods which are known in the art.

For example, the invention may use a preparation of the nucleic acid from the above mentioned samples. Such preparations include reverse transcription products and/or amplification products of such samples or nucleic acid preparations thereof. Preferably the predominant nucleic acid of the nucleic acid preparation is mRNA or cDNA obtained by reverse transcription therefrom.

Alternatively the invention may use a preparation which contains the protein material from the tissue, e.g. a lysate or homogenate of the mucosal sample.

Techniques for the isolation of nucleic acid and protein from samples, including complex samples, are numerous and well known in the art and are described at length in the literature.

The methods disclosed herein thus optionally further include the steps of manipulation, refinement or purification that are required to prepare the mucosal sample for analysis using any one or more of the above described processes, alone or in combination. In a particularly preferred embodiment the steps of obtaining RNA from said sample and/or reverse transcription of RNA from the sample are carried out.

The level of cytokine in the sample may be determined by any appropriate means, a number of which are well known and documented in the art and some of which are commercially available. The level of cytokine, or fragments thereof, in a mucosal sample can be measured by measuring the levels of nucleic acids (e.g. DNA or RNA but preferably mRNA) encoding the cytokine or by detecting the cytokine itself (i.e. at the protein level).

The level of cytokine may be expressed as an absolute amount (e.g. of protein or mRNA), an amount per unit of tissue or unit of other material (e.g. total RNA or total protein) or may be expressed as a relative measure (e.g. compared to the level of a housekeeping gene or protein or other control gene or protein).

Examples of appropriate assays for measuring the levels of nucleic acids (e.g. DNA or RNA, preferably mRNA) encoding the cytokine include amplification based methods such a RT-PCR or qRT-PCR. Examples of methods which detect the protein include immunoassays such as a radioimmunoassay (RIA) or fluorescence immunoassay, immunoprecipitation and immunoblotting or Enzyme-Linked ImmunoSorbent Assay (ELISA), with RIA and/or ELISA normally being the method of choice.

Preferred assays for the detection of cytokines at the protein level are ELISA-based assays, although RIA-based assays can also be used very effectively. Both ELISA- and RIA-based methods can be carried out by methods which are standard in the art and would be well known to a skilled person. Such methods generally involve the use of an antibody to the cytokine to be detected which is incubated with the sample to allow detection of the cytokine in the sample. Any appropriate antibodies can be used and examples of these are described in the prior art. For example, appropriate antibodies to IL-17, IFNγ and TNFα, or antibodies which recognise particular epitopes thereof can be prepared by standard techniques, e.g. by immunization of experimental animals. The same antibodies can generally be used to detect the cytokines in any immunoassay (e.g. a RIA-based assay or an ELISA-based assay), with the appropriate modifications made to the antibodies in terms of labelling etc.

Antibodies specific to TNFα may be generated by immunising an animal with polypeptide fragments of TNFα. Examples of peptides that could be used to generate specific antibodies are:

```
                                            (SEQ ID NO 1)
        ETPEGAEAKPWYEPIYLGGVQLEK (SEQ ID NO 2)
        TPSDKPVAHVVANPQAEGQLQWLNR (SEQ ID NO 3)
        ANALLANGVELR
```

In the methods of the invention, the amount of IL-17, IFNγ and/or TNFα may be determined by contacting a sample from the GI tract of said patient with an antibody that binds to the cytokine to be detected, subjecting the sample and the antibody to conditions which allow the antibody to bind and determining the amount of cytokine in said sample.

In another embodiment the amount of cytokine in the sample from the patient under investigation is determined by measuring the levels of encoding nucleic acid molecules in said sample. To this end, mRNA is commonly measured, from which gene expression levels can be inferred.

Levels of mRNA and other nucleic acid molecules can be quantitatively measured by hybridisation techniques in which the binding of a probe to the nucleic acid molecule (referred to herein as the target nucleic acid) is measured. In such cases the probe may be labelled in such a way that it can be detected directly or indirectly. After contact of such a probe with the sample under conditions which allow hybridisation, and typically following a step (or steps) to remove unbound labelled oligonucleotide and/or non-specifically bound oligonucleotide, the strength of the signal from the label of the probe emanating from the sample under investigation (i.e. the amount of label bound to the sample) will be proportional to the amount of hybridised oligonucleotide and thus to the amount of target nucleic acid. In preferred embodiments the label is selected such that it is detectable only when the probe is hybridised to its target.

In one embodiment the amount of target nucleic acid in the sample from the subject under investigation is determined by a suitable probe with a label attached thereto that will allow detection by direct means or indirect means. Alternatively, the amount of target nucleic acid may be determined by a probe which is labelled only when hybridised to its target sequence. Selective labelling may be achieved using labelled nucleotides, i.e. by incorporation into the oligonucleotide probe of a nucleotide carrying a label.

Another approach for measuring target nucleic acid abundance is based on amplification techniques. If the appropriate conditions are selected, such a reaction can be performed such that the amount of amplification product obtained will be proportional to the amount of target nucleic acid in the sample. Thus, for example, the amount of product the amplification reaction provides is proportional to the amount of the cytokine mRNA in the sample and the amount of amplification product can be used to determine the levels of the cytokine in the sample.

As mentioned previously, depending on the conditions employed, this will usually be a partially, semi- or fully quantitative measurement, but can also be a qualitative (or relative) measure in which results from a sample from a patient under investigation are simply compared to results from a control sample from the subject under investigation, with any differences between the two being noted without numerical values being affixed.

Amplification can be achieved by any convenient primer-dependent nucleic acid amplification reaction. Most conveniently the polymerase chain reaction (PCR) will be used, although the skilled man would be aware of other techniques. For instance LAR/LCR, SDA, Loop-mediated isothermal amplification and nucleic acid sequence based amplification (NASBA)/3SR (Self-Sustaining Sequence Replication) may be used.

Many variations of PCR have been developed, for instance Real Time PCR (also known as quantitative PCR, qPCR), hot-start PCR, competitive PCR, and so on, and these may all be employed where appropriate.

In one basic embodiment of the invention using a PCR based amplification an appropriate primer pair is contacted with a reaction mixture containing the sample and free nucleotides in a suitable buffer under conditions which allow hybridisation. Thermal cycling of the resulting mixture in the presence of a DNA polymerase results in amplification of the sequence characteristic of the cytokine. Optimal performance of the PCR process is influenced by choice of temperature, time at temperature, and length of time between temperatures for each step in the cycle. A typical cycling profile for PCR amplification is (a) 15 minutes of DNA melting at 95° C.; (b) 30 seconds of primer annealing at 50-65° C.; (c) 90 seconds of primer extending at 68-72° C.; (d) 30 seconds of DNA melting at 95° C.; and steps (b)-(d) are repeated as many times as necessary to obtain the desired level of amplification.

Modifications of the basic PCR method such as qPCR (Real Time PCR) have been developed that can provide quantitative information on the template being amplified. Numerous approaches have been taken although the two most common techniques use double-stranded DNA binding fluorescent dyes or selective fluorescent reporter probes.

Double-stranded DNA binding fluorescent dyes, for instance SYBR Green, associate with the amplification product as it is produced and when associated the dye fluoresces. Accordingly, by measuring fluorescence after every PCR cycle, the relative amount of amplification product can be monitored in real time. Through the use of internal standards and controls, this information can be translated into quantitative data on the amount of template at the start of the reaction.

The fluorescent reporter probes used in qPCR are sequence specific oligonucleotides, typically RNA or DNA, that have a fluorescent reporter molecule at one end and a quencher molecule at the other.

To simplify the detection of IL-17, IFNγ or TNFα expression levels in patient samples in a clinical setting, a one-step qPCr protocol in which the reverse transcription and qPCR reactions are combined within the one reaction step is preferable to traditional protocols which require a separate reverse transcription step. Methods for optimising a one-step qPCR protocol are known in the art and kits for performing one-step reactions are available commercially. To further simplify diagnosis in a clinical setting, reagents and primes for the one step qPCR procedure could be premixed within the wells of a suitable multi-well plate such as a 96 or a 384 well plate. Enzymes and primers premixed in wells could be stabilised for storage by maintaining at a low temperature such as at −20 or −80° C. and/or lyophilising the mixture in the wells. An alternative method of simplifying the one-step qPCR procedure for use in a clinical setting is to optimise the reagent as beads, whereby one bead can be added for one reaction.

To simplify the diagnostic procedure for use in a clinical setting, the qPCR protocol can be a duplex or a multiplex assay containing primers complementary to at least one of IL-17, IFNγ or TNFα and at least one housekeeping gene. Primers and fluorescent reporter probes complementary to at least one of IL-17, IFNγ or TNFα are contained within a reaction mixture comprising a reporter probe complementary to one or more housekeeping genes. Housekeeping genes are selected based on their stability in IBD vs normal intestinal mucosa. Preferably the expression levels of the housekeeping genes are similar to the expression levels of one of IL-17, IFNγ or TNFα which ever it is intended to measure in the assay in question, in intestinal mucosa.

Detection of oligo nucleotides by way of a duplex or multiplex assay is accomplished using fluorescent reporter probes which can be detected at different wavelengths for each gene to be examined. Examples of technologies suited to duplex and multiplex experiments are Scorpion® (DxS ltd.) and TaqMan® (Roche Molecular Systems, Inc.) nprobe and primer sets.

To avoid amplification and spurious detection of genomic DNA, rimers may be designed to span an exon-exon junction.

In the methods of the invention the step of determining the level of IL-17, IFNγ and/or TNFα preferably comprises:
(i) contacting the sample with oligonucleotides specific for the target sequence;
(ii) performing a primer-dependent nucleic acid amplification reaction; and
(iii) determining the amount of amplification product produced from the oligonucleotide in said primer-dependent nucleic acid amplification reaction.

If the amplification method used is itself quantitative, e.g. amplification methods in which internal standards and controls are incorporated (for instance qPCR) the method of this aspect of the invention can also provide quantitative data. In these embodiments the method can even affix a numerical value to the amount of target nucleic acid present in the sample and thus the amount of the bacteria containing said target nucleic acid in the sample. One such internal standard would be to amplify one or more (e.g. at least 2, 3, 5, or 10) samples containing a known amount of cytokine target nucleic acid under the same conditions as the test sample to provide a standard curve plotting amount of amplification product against known amount of cytokine target nucleic acid. The amount of amplification product obtained in the test sample can then be translated into a numerical value for the amount of target nucleic acid in the sample.

In other embodiments, the progress of the amplification reaction can be followed in real-time and the amplification profile can be compared with amplification profiles from samples containing known quantities of target nucleic acid or known amounts of bacteria containing said target nucleic acid. In other embodiments the cycle threshold (CT) can be used to calculate the amount of target sequence and therefore the amounts of cytokine target nucleic acid in the sample. In all qPCRs there is a threshold at which the fluorescence of the amplification product is detected above background. The cycle at which this threshold is crossed is the CT. In the exponential phase of the reaction the quantity of DNA theoretically doubles every cycle and so relative amounts of DNA can be calculated between samples by comparing CT values falling in the exponential phase. If the comparison is made with samples with a known quantity of template, the quantity of template in the test sample can be calculated and the amount of target nucleic acid present in the sample can be determined.

For any of the above methods for detecting nucleic acid molecules appropriate primers or probes can be designed based on the publicly available sequences for TNFα, IL-17 and IFNγ. The skilled person is thus able to design probes or primers for any particular application or detection method and suitable examples are set out in the Examples hereto.

The results of the analysis of samples from the patient under investigation may be compared with appropriate controls, e.g. in order to determine whether the patient has an increased level of cytokine or a "normalised" level. The comparisons may be made with a control level. Said control level may correspond to the level of the equivalent cytokine in appropriate control subjects or samples, which may be previously prepared results or standards from samples from the GI tract of subjects without IBD. The control subjects may be those with a proven history of long term remission from IBD. When the range of what is considered to be "normalised" is determined based on multiple control samples, the level of cytokines in these multiple control samples can be used to define the cut-off for normalisation. For example a cut-off for normalisation of cytokine expression in IBD patients can be defined by the upper bound of the 80, 85, 90, 95, 96, 97, 98 or 99% confidence interval (CI) for the mean cytokine level in the control samples.

Preferably the comparison will involve results from corresponding sample types, e.g. from the same or analogous region of the GI and with the same composition e.g. of tissue types. Preferably the samples will have been collected and optionally analysed for determining cytokine levels analogously.

The control level will preferably result from a combination of results obtained from multiple subjects, i.e. an average value. These may have been produced some time prior to the analysis of samples from the patient under investigation and may be provided to the practitioner digitally, e.g. on digital media or via electronic transfer to the user.

Control levels may also be referred to as "normal" levels or "reference" levels. The control level may be a discrete figure or a range. In addition, as mentioned above, such comparison with a control level, would not generally involve carrying out active tests on control subjects as part of the methods of the present invention but would generally involve a comparison with a control level which had been determined previously from control subjects and was known to the person carrying out the methods of the invention.

A combination of results obtained from multiple control subjects is particularly useful to determine what the "normalised" level is for a given cytokine. When the normalised level is determined on the basis of results from multiple subjects, the results from each subject can be used to calculate the mean cytokine level from the subjects (e.g. the subjects without IBD) and the appropriate confidence interval to be used as the cutoff level for determination of whether a given cytokine level falls within the definition of "normalised".

In a yet further aspect of the present invention is provided a kit for use in the methods described herein, said kit comprising an agent suitable for determining the level of TNFα, IL-17 or IFNγ in a GI mucosal sample. Such agent will typically have binding affinity for the cytokine of interest or for nucleic acid encoding it. Preferred agents are antibodies directed to TNFα, IL-17 or IFNγ. Other preferred agents are labelled or unlabelled oligonucleotide probes or primers suitable for detecting TNFα, IL-17 or IFNγ nucleic acid molecules. Kits may also comprise detection means and sampling means. Kit may comprise a receptacle adapted to receive a sample of GI mucosa. The kit may also comprise reaction mixtures and buffers etc. The kit may be provided with instructions, in printed or other form, which may include control values for comparison with test values obtained using the kit to perform the methods of the invention.

The invention will be further described with reference to the following non-limiting Examples with reference to the following drawings in which:

FIG. 1 shows relapse rates for CD patients after discontinuation of anti-TNFα treatment according to levels of IL-17 and TNFα mRNA levels in healed mucosa, adjusted for duration of anti-TNFα therapy (mean 34.1 weeks), generated through the Cox model. Cut-off for normalization was defined by the upper bound of mean $\Delta C_T$ values in the control patients. Panel A: Expression of IL-17. Panel B: Expression of TNF.

Figure 4:
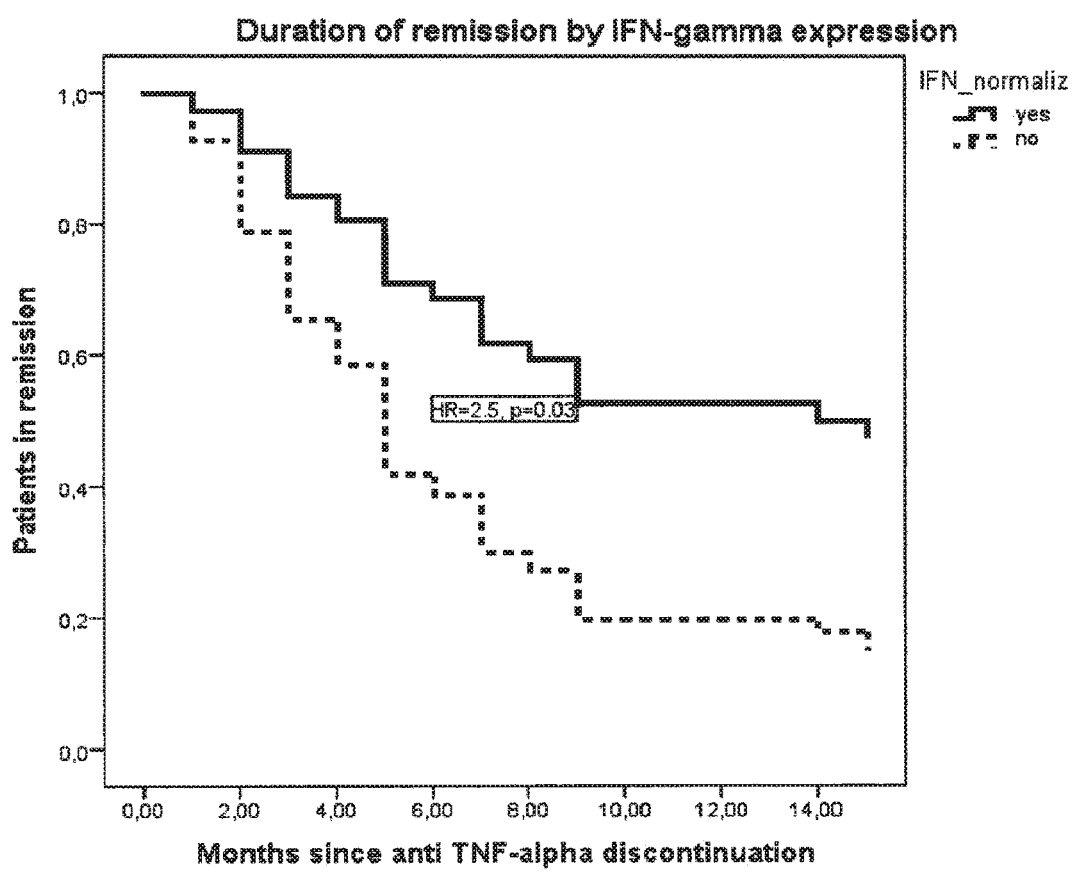

FIG. 4 shows relapse rates after discontinuation of anti-TNFα treatment according to levels of IFN-gamma mRNA in healed mucosa, adjusted for age, gender and CRP, generated through the Cox model. Cut-off for normalization was defined by the upper bound of mean $\Delta C_T$ values in the control patients. 75% of the patients with high expression of post IFN-gamma mRNA have a relapse within the first 12 months, while 50% of the patients with low IFN-gamma mRNA have a relapse (cox-regression, odds ratio=2 (95% CI 1.0-3.7), p-value<0.05).

EXAMPLES

Example 1

Predictive Value of Cytokine Gene Expression Levels for Long Term Remission after Discontinuation of anti TNFα therapy in CD Methods Patients This prospective trial was conducted between September 2008 and April 2012 and was part of the prospective Tromsø-study on IBD. In short, the treatment algorithm is based on induction of remission by targeted therapy until endoscopic healing, followed by withdrawal of biological therapy, in order to define criteria for discontinuation. Patients with established and active CD, defined as Crohn's Disease Activity Index (CDAI) score above 150 (Best W R, Becktel J M, Singleton J W, Kern F, Jr. Development of a Crohn's disease activity index. National Cooperative Crohn's Disease Study. *Gastroenterology* 1976; 70(3):439-444) and/or active disease judged by endoscopy with ulcerations despite conventional therapy, who obtained documented complete endoscopic healing upon receiving anti-TNFα induction therapy, were included in the study. Patients were given adalimumab (HUMIRA®; Abbott laboratories, Abbott Park, Ill., USA): 80 mg at week 0 followed by 40 mg every 2 weeks for a minimum of 10 weeks, or infliximab 5 mg/kg (REMICADE®; Centocor Ortho Biotech Inc., Horsham, Pa., USA) for a minimum of 3 infusions (at weeks 0, 2 and 6). Prolonged induction treatment was given until documentation of complete endoscopic healing, every 2 weeks with adalimumab and every 4 weeks with infliximab. After anti-TNFα discontinuation patients were followed until relapse. Seventeen patients undergoing colonoscopy for reasons other than IBD with normal endoscopic findings and normal colonic histological findings served as controls. All participants signed an informed written consent. The Regional Committee of Medical Ethics of North Norway and the Norwegian Social Science Data Services approved of the study and the storage of biological material.

Definitions of Response to Treatment and Relapse

Clinical remission was defined as reduction of the CDAI score to less than 150 (Best et al supra). Endoscopy was performed when clinical remission was achieved. Mucosal healing at endoscopy was defined as complete mucosal restitution with absence of ulceration and erythema. If mucosal healing had not been obtained, patients were treated for another 3 months before the next endoscopy was performed. Anti-TNFα therapy was discontinued upon documentation of mucosal healing. Relapse was defined as CDAI increase of >70 points from the time of discontinuation, and/or endoscopic findings qualifying for re-treatment with an anti-TNFα agent or use of systemic steroids. Relapse was declared by the gastroenterologists performing the endoscopic examination or patient consultation.

Tissue Samples

Biopsies were sampled according to the patient's phenotype from the colon or terminal ileum during endoscopy of patients in complete endoscopic healing. Biopsy specimens for real-time PCR were immediately immersed in RNAlater (Ambion Inc, Austin, USA).

Cytokine Measurements

Pre-PCR and Real-Time PCR Procedures

Real-time PCR procedures used in this study have previously been described in detail (Cui et al, 2006, Scand J Clin Lab Invest 66(3):249-59). In short, RNA was isolated from biopsies by the Promega method (Promega Corporation, Madison, Wis., USA). Total RNA concentration was measured by NanoVue spectrophotometer (GE Healthcare, Piscataway, N.J., USA). Reverse transcription of total RNA was performed by iScript (Bio-Rad, Hercules, Calif., USA) according to the manufacturer's instructions. Levels of mRNA for IL-17, IL-23, IFNG, TNF, IL-10, FOXP3 and β-Actin (ACTB, house-keeping gene) were determined in duplicates by real-time quantitative RT-PCR using TaqMan chemistry (Applied Biosystems, Foster City, Calif., USA) and a standardized threshold value. In our hands the quantitative PCR method detected a difference of 24% with 95% confidence over a 5 log 10 range {Goll, 2006 30/id}. Except for the IFNG assay (Applied Biosystems, Ref No. Hs00174143_m1), all assays were in-house; primer sequences have been published in previous reports {Olsen, 2011 98/id}{Goll, 2007 81/id}{Rismo, 2012 116/id}. Stability of ACTB as housekeeping gene was investigated by running analysis of variance (ANCOVA) on all ACTB $C_T$ values with age, gender and endoscopic healing/control as factors/covariates; no significant effects on beta-actin expression levels were found. The cytokine values were expressed and analyzed according to the $\Delta C_T$ and the $\Delta \Delta C_T$ method (fold change=$2^{-\Delta\Delta C_T}$), applied as appropriate {Schmittgen, 2008 31/id}. The laboratory investigators were blinded to the clinical data.

Statistics

Frequency distribution analysis and tests of normality were run on all subgroups. The $\Delta C_T$ values from real-time PCR resembled normal distribution patterns, except for IL-23 in CD patients, IFNG in the controls and IL-10 in CD patients. Categorical data was analysed by Pearson Chi-Square or Fischer's exact test, as appropriate. Continuous data were analyzed by t-test for independent samples, ANCOVA adjusted for age, or Mann-Whitney U-test, as appropriate. Estimated CT differences from the ANCOVA analysis or t-test were converted to fold differences in cytokine gene expressions (fold change=$2^{-\Delta\Delta C_T}$). Time to relapse was analysed using Kaplan-Meier survival analysis. Factors related to time to relapse were analyzed by Cox proportional hazard regression analysis. Clinical, demographical and immunologic variables were analyzed using univariate Cox regression and considered for multivariate Cox regression, but due to the small sample-size and loss of power, the number of covariates we were able to include in each model was limited. Immunological factors were analysed as "normalization/not normalization", and survival plots generated by the Cox regression model are presented for these categories. All statistical analyses were performed in PASW (SPSS) Statistics 18.0 (IBM Corporation, Armonk, N.Y., USA).

Results

Study population

Adalimumab or infliximab was administered to 84 CD patients with intestinal lesions verified during endoscopic examination of the colon or terminal ileum and CDAI above 150. Clinical remission was achieved in 68 patients, and 57 of these patients underwent an endoscopic examination, reasons for not performing endoscopy were mainly patient related (lost to follow-up, refusal). Complete endoscopic healing was documented in 41 of these patients and tissue samples were provided for real-time PCR analyses, 62% (23) and 38% (14) of samples were collected from the colon and terminal ileum, respectively. There were no significant differences in cytokine mRNA levels between samples collected from the colon compared to the terminal ileum; no tendencies were observed (data not shown). Four patients did not discontinue anti-TNFα therapy upon mucosal healing and were excluded from this follow-up study. Thirty-seven patients with documented healing discontinued anti-TNFα therapy and entered the follow-up study; 30 had received adalimumab and 7 infliximab. Characteristics of all included CD patients and controls are presented in Table 4. Mean age in the control group was significantly higher than for the CD patients (p<0.001).

TABLE 4

Characteristics of patients with Crohn's disease with healed mucosa entering follow-up, and controls

| Characteristic | Patients (N = 37) | Controls (N = 17) | p-value |
|---|---|---|---|
| Male | 18 (49%) | 8 (47%) | 0.91 |
| Age, years | 39.2 (17-70) | 56.6 (36-68) | <0.001 |
| Disease duration, years (median (range)) | 8.5 (0.5-35) | | N.A |
| Duration of anti-TNFα therapy, weeks (median (range)) | 20 (8-124) | | N.A |
| Active smoking | 13 (35%) | 2 (12%) | 0.18 |
| CDAI | 55.0 (6-140) | | N.A |
| Involved intestinal area | | | N.A |
| Terminal ileum (L1) | 6 (16%) | | |
| Colon (L2) | 15 (41%) | | |
| Ileocolonic (L3) | 16 (43%) | | |
| Biopsy | | | |
| Colon | 23 (62%) | 17 (100%) | N.A |
| Terminal ileum | 14 (38%) | | |
| Medication | | | N.A |
| Corticosteroids | 0 (0%) | | |
| AZA/MTX | 31 (84%) | | |
| 5-ASA | 4 (11%) | | |
| None | 6 (16%) | | |
| AZA/MTX during observation | 32 (86%) | | N.A |

Data are presented as n (%) or mean (range) except where otherwise stated.
Abbreviations: N.A = not applicable, CDAI = Crohn's disease activity Index, L1/L2/L3 = disease location according to the Montreal classification, AZA = Azathioprine, MTX = Methotrexate, 5-ASA = 5-aminosalicylates Outcome After Discontinuation of Anti-TNFα Therapy Follow-up time ranged from 3 to 176 weeks, with the earliest relapse registered by CDAI increase 3 weeks into follow-up. Median time to relapse was 26 weeks. At 26 weeks 15 (48%) of 31 evaluated patients were in remission, and 7 (26%) of 27 evaluated patients were still in remission at week 52. A total of 23 relapses was declared; 16 prior to week 26, accumulating to 20 by week 52 (74%). Six patients had shorter follow-up time than 26 weeks at study closing date.

Normalization of Cytokine Expression Levels and Time to Relapse

Mucosal gene expression of IL-17, TNF, IL-10 and FOXP3 were significantly higher in healed CD mucosa compared to controls, whereas IL-23 and IFNG levels were not significantly different from controls (Table 5). Cut-off for normalization of cytokine gene expression in CD patients was defined by the upper bound of the 95% CI for mean $C_T$ value of each cytokine measured in samples from control patients. Of 37 patients, 12 had normalized IL-17 expression levels at time of mucosal healing, whereas 10 had normalized TNFα expression levels. Only 6 patients had normalization of both IL-17 and TNF. Pearson's correlation analysis showed that IL-17 and TNFα gene expression levels were significantly correlated (r=0.701, p<0.001).

All patients with normalized TNFα mRNA expression and 88% of evaluated patients with normalized IL-17 mRNA expression were still in remission at week 26, whereas without normalization of TNFα and IL-17, only 24% and 35% of patients, respectively, were still in remission at this time-point (table 2). After 52 weeks, 63% and 67% of evaluated patients with normalized TNFα and IL-17 gene expression levels, respectively, were still in remission. Without normalized TNFα and IL-17 mRNA expression levels, only 11% and 14% of evaluated patients, respectively, were still in remission at 52 weeks (table 6).

TABLE 5

Comparison of cytokine expression in Crohn's patients with healed mucosa after anti-TNFα therapy versus healthy controls

|  | IL-17 | IL-23 | IFNG | TNF | IL-10 | FOXP3 |
|---|---|---|---|---|---|---|
| Crohn's vs controls | 6.5 | 1.9 | 1.5 | 3.9 | 2.5 | 4.8 |
| (p-value) | (0.006) | (0.175)# | (0.513)# | (0.002) | (0.002)# | (<0.001) |

Abbreviations: IL = Interleukin, IFN = Interferon, TNF = Tumour necrosis factor, FOXP3 = Forkhead Box P3
Numbers refer to fold difference in cytokine expression levels between groups. Estimates and p-values were derived from ANCOVA adjusted for age and the #Mann-Whitney U-test for non-parametric data

TABLE 6

Relapse rates at week 26 and 52 according to category of cytokine expression level in healed mucosa of patients with Crohn's disease.

|  | Evaluation week 26 (N = 31) | | | Evaluation week 52 (N = 27) | | |
|---|---|---|---|---|---|---|
|  | Relapse (n = 16) | Remission (n = 15) | p | Relapse (n = 20) | Remission (n = 7) | p |
| TNFα expression | | | | | | |
| Normalization | 0 (0%) | 10 (100%) | <0.001 | 3 (37%) | 5 (63%) | 0.01 |
| Not normalization | 16 (76%) | 5 (24%) |  | 17 (89%) | 2 (11%) |  |
| IL-17 expression | | | | | | |
| Normalization | 1 (12%) | 7 (88%) | 0.015 | 2 (33%) | 4 (67%) |  |
| Not normalization | 15 (65%) | 8 (35%) |  | 18 (86%) | 3 (14%) | 0.02 |

Abbreviations: TNF = Tumour necrosis factor, IL = Interleukin, P-values were derived from Fischer's Exact Test.

Cytokine mRNA Expression in Patients Relapsing before 26 and 52 Weeks

There were no significant differences in demographic and clinical data among patients relapsing before 26 or 52 weeks or not (data not shown). Differences in mucosal mRNA expression of IL-17, TNF, IL-10 and FOXP3 between patients with and without relapse at week 26 and 52 are presented in table 7. Expression of IL-17, TNFα and FOXP3 was significantly higher in the sub-group of patients who had relapsed before 26 weeks and 52 weeks than those who had not relapsed at these evaluations.

TABLE 7

Comparison of mucosal cytokine expression in patients with and without relapse at week 26 and 52, expressed as fold differences

|  | IL-17 | TNF | IL-10 | FOXP3 |
|---|---|---|---|---|
| Relapse <26 wks vs no relapse at 26 wks | 6.7 | 6.2 | 2.5 | 3.1 |
| (p-value) | (0.009) | (<0.001) | (0.06) | (0.02) |
| Relapse <52 wks vs no relapse at 52 wks | 6.4 | 3.5 | 2.1 | 4.0 |
| (p-value) | (0.04) | (0.04) | (0.21) | (0.02) |

The real-time PCR data followed normal distribution patterns and no clinical characteristics were significantly different between the subgroups; estimates and p-values were derived from t-test for independent samples Survival Analysis and Predictive Ffactors of Relapse Survival analyses by category of IL-17 and TNFα expression revealed significant differences in median time to relapse for patients with and without normalized levels. Median time to relapse was 20 and 68 weeks for patients with elevated and normalized expression levels of IL-17, respectively (p=0.02, log-rank). Median time to relapse by category of TNFα expression was also 20 and 68 weeks for the elevated and normalized expression level groups, respectively (p=0.003, log-rank).

Figure 1:
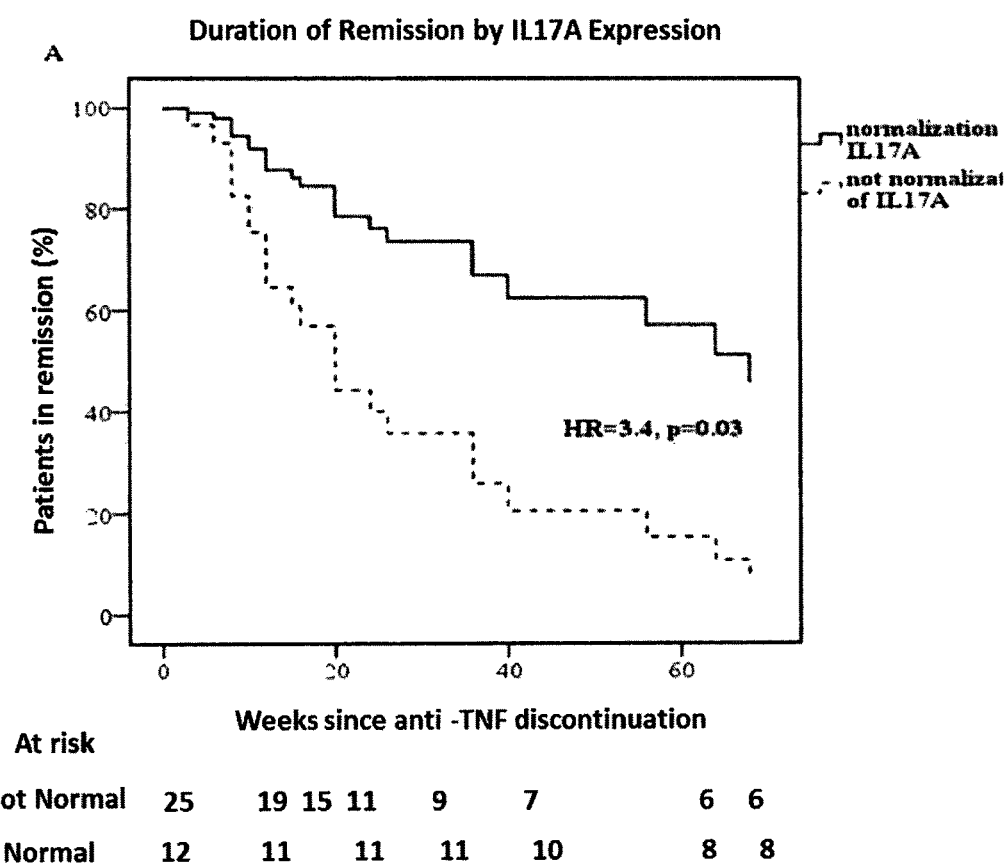
Figure 1:
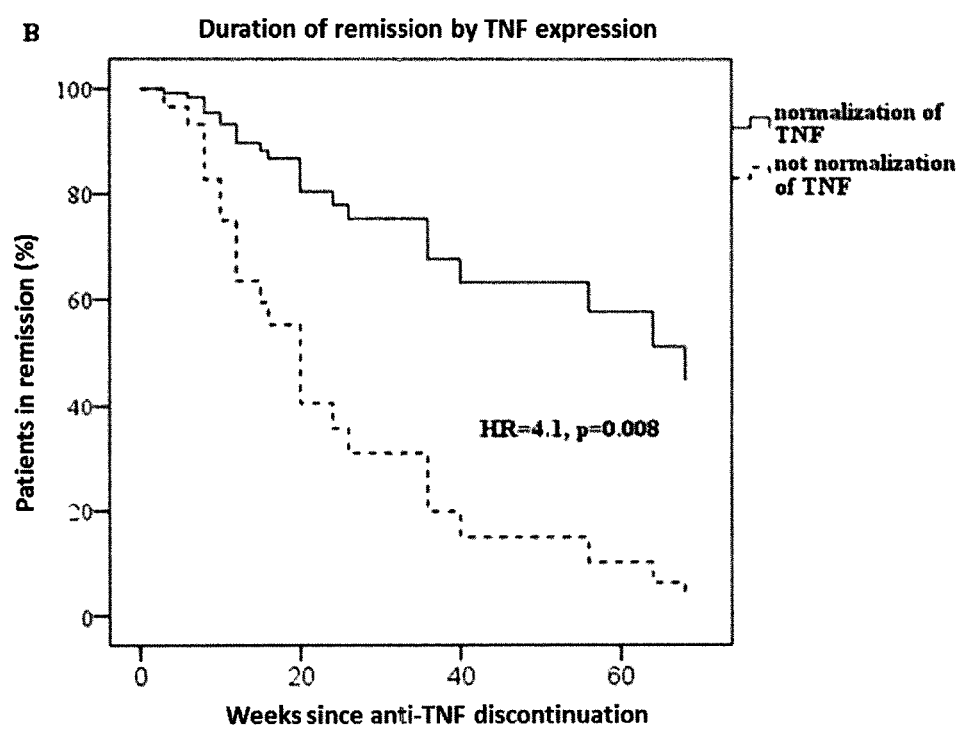

By univariate Cox proportional hazards regression analyses possible risk factors of relapse including demographic and clinical as well as cytokine expression levels categorized as normalized/not normalized, were assessed (Table 8). Only lack of normalization of IL-17 and TNFα was significantly associated with relapse in the univariate analyses (HR=3.3, p=0.03 and HR=4.3, p=0.007, respectively). Considering the large range of duration of anti-TNFα therapy, we adjusted for this in the Cox regression analyses. Adjusted for duration of therapy (mean 34.1 weeks), lack of normalization of IL-17 and TNFα still significantly increased the risk of relapse compared to patients with normalized expression levels (HR=3.4, p=0.03 and HR=4.1, p=0.008, respectively). Analyses for adalimumab treated patients only (n=30) also demonstrated a significant association between elevated levels of IL-17 and TNFα and risk of relapse, univariately as well as adjusted for duration of therapy (HR=3.3, p=0.04 and HR=3.2, p=0.03, respectively). Due to the small sample sizes extensive multivariate analyses were not appropriate, and sub-analyses for infliximab treated patients (n=7) were not performed. Survival plots from the Cox regression models are presented in FIG. 1, panels A and B.

TABLE 8

Variables associated with risk of relapse after discontinuation of anti-TNFα therapy in patients with Crohn's disease

| Variable | HR | p-value | 95% CI of HR |
|---|---|---|---|
| Age (10 year increments) | 0.8 | 0.14 | 0.61-1.08 |
| Male gender | 1.5 | 0.34 | 0.66-3.43 |
| Disease duration (per year) | 1.01 | 0.61 | 0.97-1.06 |
| Duration of anti-TNFα therapy | 1.01 | 0.37 | 0.99-1.02 |
| Active smoking | 1.4 | 0.45 | 0.59-3.27 |
| CDAI at endoscopy | 1.01 | 0.37 | 0.99-1.02 |
| Disease extension | | | |
| L1 (ileum) | 0.8 | 0.62 | 0.25-2.24 |
| L2 (colon) | 0.9 | 0.85 | 0.40-2.13 |
| L3 (ileocolonic) | 1.3 | 0.53 | 0.57-2.99 |
| AZA/MTX at baseline | 2.6 | 0.14 | 0.74-8.99 |
| AZA/MTX during follow-up | 0.6 | 0.40 | 0.17-2.02 |
| Elevated IL-17 | 3.3 | 0.03 | 1.11-9.95 |
| Elevated TNF | 4.3 | 0.007 | 1.49-12.14 |
| Elevated FOXP3 | 1.9 | 0.18 | 0.74-4.71 |
| Elevated IL-10 | 1.7 | 0.29 | 0.65-4.27 |

Abbreviations: HR = Hazard ratio, CI = Confidence Interval, CDAI = Crohn's Disease Activity Index, L1/L2/L3 = According to the Montreal classification, AZA = Azathioprine, MTX = Methotrexate, IL = Interleukin, TNF = Tumour necrosis factor, FOXP3 = Forkhead Box P3

Receiver Operating Characteristics

Cut-off for normalization was based on cytokine gene expression levels in the group of non-IBD controls. ROC analyses showed that lack of normalization of IL-17 and TNFα gene expression predicted risk of relapse with sensitivity of 81% and 80% for IL-17 and TNF, respectively (Area under curve (AUC)=0.752, p=0.014 and AUC=0.654, p=0.13, respectively) and specificity of 61.5% and 38.5%, respectively. Selection of a cut-off that would increase the sensitivity to above 90% for IL-17 and TNFα reduced the specificity to 38.5% and 23%, respectively.

Conclusion

Normalization of pro-inflammatory cytokine expression levels does not occur in all patients with healed mucosa after treatment with anti-TNFα agents. A large proportion of CD patients relapse within one year after discontinuation of anti-TNFα therapy, but the prognosis seems to be favourable in patients who have normalized gene expression levels of TNFα and IL-17.

Example 2

Predictive Value of Cytokine Gene Expression Levels for Long Term Remission after Discontinuation of Anti TNFα Therapy in UC Hundred and twenty-four patients with moderate to severe ulcerative colitis were treated with Infliximab. Infliximab 5 mg/kg (REMICADE®; Centocor Inc., Horsham, Pa., USA) was given as repeated infusions at 0, 2 and 6 week and then every 4 weeks until remission. Only patients receiving 3 or more infusions followed by an endoscopic examination were included. Eighty-five (64%) patients achieved clinical and endoscopic remission after induction therapy and biopsies were taken in fifty patients for measurements for further analysis. Evaluation of response was performed by clinical examination and colonoscopy 2-6 weeks after the last IFX infusion. Remission was defined by reduction of the UCDAI score to less than 3 in addition to a reduction of the endoscopic sub-score to 0 or 1 (D'Haens G et al. Gastroenterology 2007; 132:763-86). The patients were followed-up with regular clinical evaluations. Relapse was defined using endoscopic and clinical disease activity indices (UCDAI-score>3 end endoscopic score>1). Early relapse was defined as relapse within 12 months. The patients were followed-up in a period of 12-36 months. Demographic data and medication list are listed in table 9 and table 10. The diagnoses were based on established clinical, endoscopic and histological criteria (Sands BE. Gastroenterology 2004, 126(6):1518-32).

The degree of illness in UC patients was evaluated using ulcerative colitis disease activity index (UCDAI) which is based on clinical signs (score 0-12) and on endoscopic evaluation of the distal colon during colonoscopy (grade 0-3) (Sutherland L R, Gastroenterology 1987, 92(6):1894-8). Samples from subjects with normal colonoscopy and normal colonic histological examination served as controls. All participants were informed and signed a written consent. The Regional Committee of Medical Ethics of North Norway and the Norwegian Social Science Data Services approved of the storage of biological material.

TABLE 9

Demographic data

| N = 50, Female 19/male 31 | Mean | Range |
|---|---|---|
| Age | 37 | (15-70) |
| Time of disease before IFX treatment | 5.1 years | (0-17) |
| Baseline CRP | 13 | (0-97) |
| UCDAI before IFX | 10 | (6-12) |
| UCDAI after IFX | 1.5 | (0-2) |
| Endoscopic pre-score | 2.7 | (1-3) |
| Endoscopic post-score | 0.6 | (0-1) |
| Doses of IFX | 3.7 | (2-9) |
| Pre-calprotectin | 1654 | (0-2500) |
| Post-calprotectin | 226 | (0-2345) |

TABLE 10

| | Yes | No | Earlier (no data) |
|---|---|---|---|
| Smoke | 7 | 25 | 1 (4) |
| ASA | 30 | | |
| Azathioprine (AZA) | 45 | | |
| Steroids | 8 | | |
| Steroids and 5ASA | 6 | | |
| 5ASA and AZA | 14 | | |
| Steropids, 5ASA, AZA | 2 | | |

Tissue Samples

Colonic mucosal biopsies were sampled from the region with most severely inflammation. Biopsy specimens for RNA extraction were immediately immersed in RNA later (Ambion Inc, Austin, USA) and stored at 4° C. overnight.

Cytokine Measurements
Pre-PCR and Real-Time PCR Procedures.

Real-time PCR procedures have previously been described in detail (Olsen T et al. Scand J Gastroenterol 2007 November; 42(11):1312-20) and (Cui G et al. Scand J Clin Lab Invest 2006, 66. 249-59). RNA was extracted from biopsies by the Trizol method (Invitrogen, Paisley, UK). Total RNA concentration was measured at 260 nm with U-1500 UV/Vis spectrophotometer (Hitachi Instruments Inc, San Jose, Calif., USA). An Agilent 2100 Bioanalyzer was used to measure RNA integrity with RNA 6000 Nano chips (Agilent Technology, Inc, Böblingen, Germany) according to the manufacturer's instructions. The RIN values were above 8 (Cui G et al. Scand J Clin Lab Invest 2006, 66. 249-59).

Reverse transcription of total RNA was performed by iScript (Bio-Rad, Hercules, Calif., USA) according to the manufacturer's instructions. Levels of mRNA for TNF-α, IL-17, IL-23, IFN-γ, TGF-β, IL-6 and beta-actin (housekeeping gene) were determined in duplicates by real-time quantitative RT-PCR using TaqMan chemistry (Applied Biosystems, Foster City, Calif., USA) and a standardized threshold value. Evaluations of pre-PCR steps and assays have earlier been conducted in order to prevent methodological pitfalls that have been linked to this method (Cui G et al. Scand J Clin Lab Invest 2006, 66. 249-59). In our hands the quantitative PCR method detects a difference of 24% with 95% confidence over a $5_{log}$ range (Goll R et al. BMC Bioinformatics 2006; 7:107). Except for the IFN-gamma assay, all assays were in-house; primer sequences are listed in table 2. Stability of beta-actin (ACTB) as housekeeping gene in the present context has been ascertained earlier (Olsen T et al. Scand J Gastroenterol 2007 42(11):1312-20.) The cytokine values were expressed and analyzed according to the delta-delta-CT method (fold change=$2^{-\Delta\Delta C_T}$) (Schmittgen T D et al Nat Protoc 2008; 3(6):1101-8). Expanding the equation to its full form: $2^{-\Delta\Delta C_T}=[(C_T$ gene of interest$-C_T$ internal control) sample A$-(C_T$ gene of interest$-C_T$ internal control) sample B)]. The laboratory investigators were blinded to clinical data.

TABLE 11

Primer sequences

| Genbank Id | Forward primer sequence 5'- 3' Reverse primer | Probe sequence 5' - 3' Conjugation | Reference sequence |
|---|---|---|---|
| TNFα | CACGCTCTTCTGCCTGCTG (SEQ ID NO 4) GATGATCTGACTGCCTGGGC (SEQ ID NO 5) | CCAGAGGGAAGAGTTCCCCAGGGAC (SEQ ID NO 6) | Goll et al 2007 Helicobacter 12: 185-192 |
| IL-17 | TGATTGGAAGAAACAACGATGACT (SEQ ID NO 7) ATTGTGATTCCTGCCTTCACTATG (SEQ ID NO 8) | TGGTGTCACTGCTACTGCTGCTGAGC (SEQ ID NO 9) FAM-BHQ | NM_002190.2 |
| IL-23A | CCCAAGGACTCAGGGACAAC (SEQ ID NO 10) TCCTAGCAGCTTCTCATAAAAATCA (SEQ ID NO 11) | TCAGTTCTGCTTGCAAAGGATCCACCAG (SEQ ID NO 12) FAM-BHQ | NM_016584.2 |
| IL-6 | CCAGGAGCCCAGCTATGAAC (SEQ ID NO 13) CCCAGGGAGAAGGCAACTG (SEQ ID 14) | CCTTCTCCACAAGCGCCTTCGGT (SEQ ID NO 15) FAM - TAMRA | NM_000600.3 |
| TGFB1 | CTGCTGAGGCTCAAGTTAAAAGTG (SEQ ID NO 16) TGAGGTATCGCCAGGAATTGT (SEQ ID NO 17) | CAGCACGTGGAGCTGTACCAGAAATACAGC (SEQ ID NO 18) FAM - BHQ | NM_000660.3 |
| IFNG | Assay design from Applied Biosystems Ref no. Hs00174143_m1 | | |

Statistical Analysis

To compare the differences within a group the Student paired t-test was used for normally distributed data and the Wilcoxon signed rank sum test for non-normally distributed data. Analysis of variance (ANCOVA) or the Kruskal-Wallis ANOVA on ranks was used to access the differences between the groups, as appropriate. Estimated $C_T$ differences from the ANCOVA analysis were then converted to fold differences in cytokine gene expressions. Categorical data were analyzed by the $\chi 2$-test or by logistic regression when appropriate.

Time to relapse was analysed using Kaplan-Meier survival analysis. Factors related to time to relapse were analyzed by Cox proportional hazard regression analysis. Clinical, demographical and immunologic variables were analyzed using Cox regression and considered for multivariate Cox regression, but due to the small sample-size and loss of power, the number of covariates we were able to include in each model was limited. Immunological factors were analysed as "normalization/not normalization", and survival plots generated by the Cox regression model are presented for these categories. P-values below 0.05 were considered significant. UCDAI scores defined outcome and relapse. Post-treatment remission was strictly defined as UCDAI less than 3 with endoscopic sub score of 0 or 1. All statistical analyses were performed in PASW Statistics.

Results
Study Population

Of the fifty patients in endoscope and clinical remission after IFX induction treatment, 60% (30/50) had a relapse within 12 months while 40% (20/50) maintained a clinical and endoscopic remission after a year. Demographical and clinical data in the two subgroups are presented in table 12. Post-CRP is missing because blood samples were not taken of the patients in remission after successful IFX-treatment. Pre-CRP was significant higher in the early relapse group compared to the group in remission (table 12, p-value<0.05) and therefore included as a covariate in the Cox-regression analysis. No other clinical or demographic data were significant different in the two subgroups.

TABLE 12

| Patients characteristics | Remission n = 20 | Relapse n = 30 | p-values |
|---|---|---|---|
| Age at first infusion (median/(range)) | 37 (15-62) | 37 (15-70) | 0.8 |
| Gender (Male/Female) | 10 M/10 F | 21 M/9 F | 0.1 |
| Disease duration in years (median/(range)) | 5.4 (0.5-14) | 5 (0.5-17) | 0.7 |
| Active smoking | 5 | 2 | 0.4 |
| Pre-IFX medication (no) | | | |
| Steroids (alone or in combination) | 8 | 10 | 0.46 |
| 5-ASA (alone or in combination) | 11 | 19 | 0.57 |
| AZA/MTX (alone or in combination) | 4 | 9 | 0.69 |
| Pre-treatment UCDAI (mean/(range)) | 10.25 (6-12) | 10.1 (7-12) | 0.73 |
| Post-treatment UCDAI (mean/(range)) | 1.5 (0-2) | 1.5 (0-2) | 0.9 |

TABLE 12-continued

| Patients characteristics | Remission n = 20 | Relapse n = 30 | p-values |
|---|---|---|---|
| Pre-treatment Endoscopic score (mean/(range)) | 2.6 (1-3) | 2.8 (2-3) | 0.5 |
| Post-treatment Endoscopic score (mean/(range)) | 0.6 (0-1) | 0.6 (0-1) | 0.9 |
| Pre-CRP (mean/range) | 22 (0-97) | 7 (0-54) | 0.002* |
| Pre-Calprotectin | 1588 (0-2500) | 1707 (22-500) | 0.98 |
| Post-Calprotectin | 140 (0-982) | 287 (0-2345) | 0.2 |

Abbreviations: No = number of patients, IFX = Infliximab, 5-ASA = 5-aminosalicylates, AZA = Azathiopurine, MTX = Methotrexate, CRP = C-reactive protein, UCDAI = Ulcerative Colitis Disease Activity Index, N.A = not applicable
Statistical tests: for categorical data; Pearsons Chi square or Fisher's exact test as appropriate, for continuous data; t-test or Mann-Whitney U test as appropriate.

Cytokine mRNA Expression in Patients Relapsing before 6, 12 and After 24 Months

Analysis of mean differences (ANCOVA) was performed for the gene expression in UC patients achieving remission, early relapse and controls (table 13 and table 14). In table 13 relapse rates of relapse according to normalized and not normalized cytokine expression at weeks 26, 52 and 104, respectively, are shown Moreover, the cytokine mRNA expression in healed mucosa of TNF-α, IL-17 and IFN-γ were significantly higher in UC patients who relapsed within 12 months compared to controls (2.5, 3.7 and 4 fold difference in CT-values relative to each other, p-values<0.05 in all, table 14). This applies both to patients who achieved remission after 3 IFX infusions and patients who did not. The mucosal gene expressions of TNF-α, IL-17 and IFN-gamma in healed mucosa were also significantly higher in patients who relapsed within 6 and 24 months compared with patients achieving remission (table 14).

TABLE 13

Relapse rates at week 26 and 52 according to category of cytokine expression level in healed mucosa of patients with Ulcerative Colitis

| | Evaluation Week 26 | | | Evaluation Week 52 | | | Evaluation Week 104 | | |
|---|---|---|---|---|---|---|---|---|---|
| | Relapse N = 23 | Remission N = 27 | p= | Relapse N = 31 | Remission N = 19 | p= | Relapse N = 34 | Remission N = 16 | p= |
| TNFα expression | | | | | | | | | |
| Normalization | 7 (30%) | 15 (55%) | | 11 (35%) | 11 (58%) | | 13 (38%) | 9 (56%) | |
| Not normalization | 16 (70%) | 12 (44%) | 0.05 | 20 (64%) | 8 (40%) | 0.06 | 21 (62%) | 7 (44%) | 0.1 |
| IL-17 expression | | | | | | | | | |
| Normalization | 4 (31%) | 9 (69%) | 0.09 | 8 (61%) | 5 (39%) | 0.3 | 9 (69%) | 4 (31%) | 0.3 |
| Not normalization | 18 (60%) | 12 (40%) | | 21 (70%) | 9 (30%) | | 23 (77%) | 7 (23%) | |
| IFN-gamma expression | | | | | | | | | |
| Normalization | 4 (22%) | 14 (78%) | 0.004 | 10 (52%) | 9 (50%) | 0.04 | 11 (61%) | 7 (39%) | 0.03 |
| Not normalization | 14 (78%) | 4 (26%) | | 9 (48%) | 11 (58%) | | 16 (39%) | 3 (16%) | |

TABLE 14

Comparison of mucosal cytokine expression in patients with and without relapse at week 26, 52 and 104, expressed as fold differences

|  | IL-17<br>N = 46 | TNFα<br>N = 49 | IL-23<br>N = 47 | IFN-y<br>N = 39 | TGF-β<br>N = 25 | IL-6<br>N = 25 |
|---|---|---|---|---|---|---|
| Relapse < 26 weeks vs no relapse (p-value) | 4 (0.01) | 1.8 (0.03) | 1.5 (0.3) | 6.9 (0.001) | 1.6 (0.07) | 1.07 (0.9) |
| Relapse < 52 weeks vs no relapse | 3.7 (0.03) | 2.5 (0.009) | 1 (0.7) | 4 (0.04) | 1.4 (0.1) | 1.07 (0.9) |
| Relapse < 104 weeks vs no relapse | 4 (0.01) | 2.3 (0.01) | 1.2 (0.6) | 4 (0.03) | 1.07 (0.3) | 1.07 (0.9) |

The gene expression levels in colon mucosa were measured by quantitative realtime PCR. For patients in remission and non-remission, values are expressed as fold difference (p-value) relative to each other. Estimates and p-values were derived by ANCOVA with correction for sex and age. Sidak post hoc analysis were used for correction type II errors Time to Relapse and Survival Analyses Cut-off for normalization of cytokine gene expression in UC patients was defined by the upper bound of the 95% CI for mean $C_T$ value of each cytokine measured in samples from control patients. Of 50 patients, 22 had normalized TNF-α expression levels at time of mucosal healing, whereas 15 had normalized IL-17 expression levels and 20 had normalized IFN-gamma expression levels.

Figure 2:
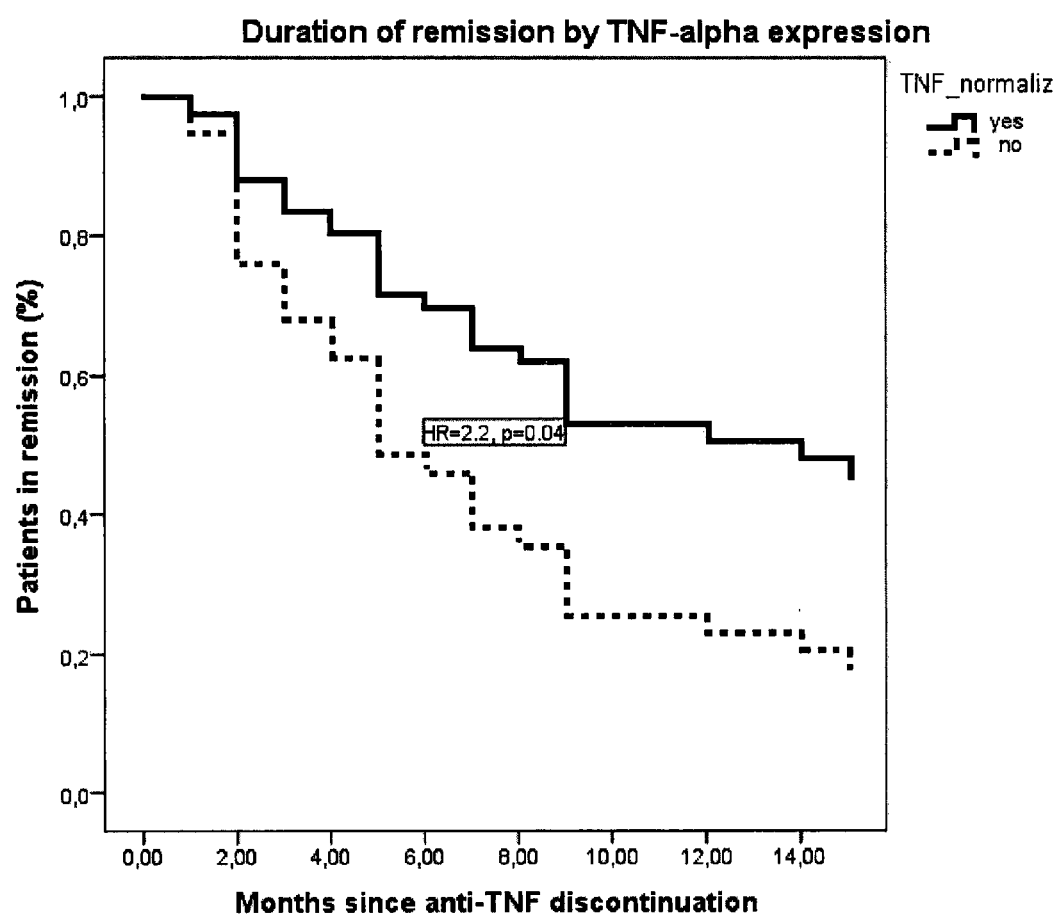
FIG. 2 shows relapse rates in UC patients after discontinuation of anti-TNFα treatment according to levels of TNFα mRNA in healed mucosa, adjusted for age, gender and CRP, generated through the Cox model. Cut-off for normalization was defined by the upper bound of mean $\Delta C_T$ values in the control patients.
Figure 3:
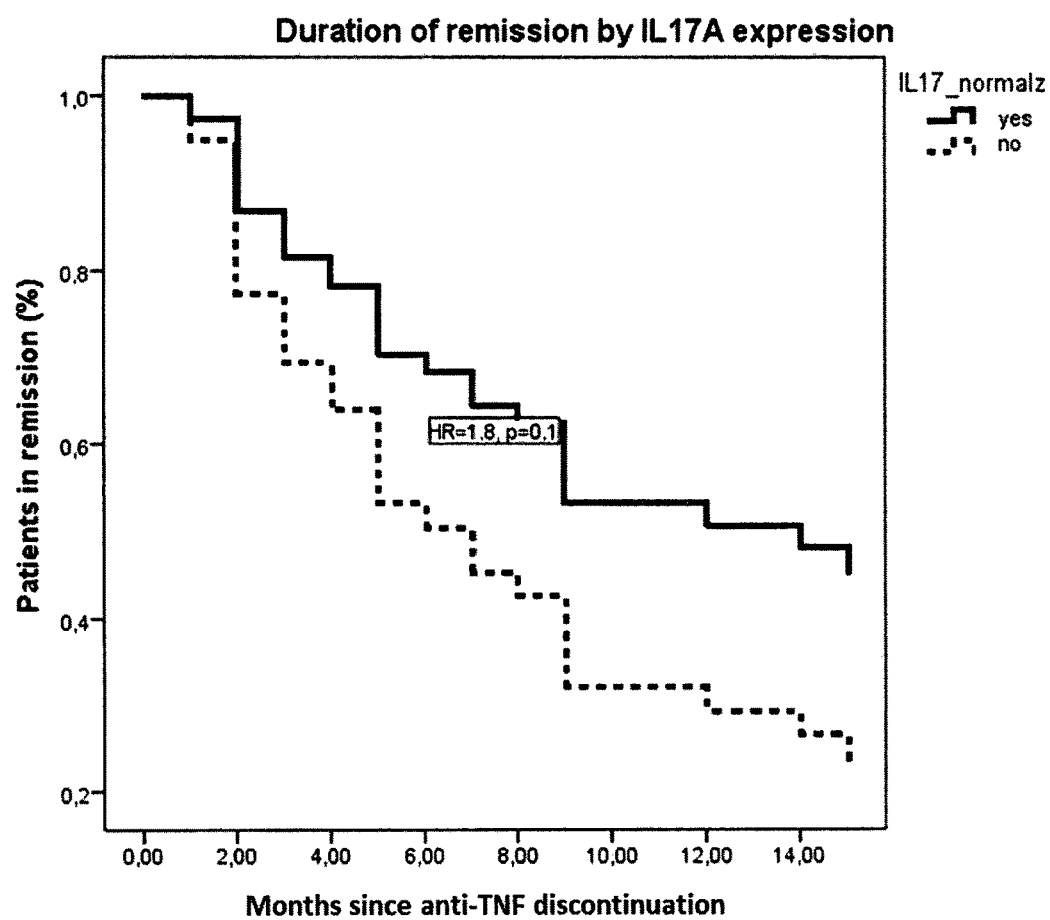
FIG. 3 shows relapse rates in ulcerative colitis after discontinuation of anti-TNFα treatment according to levels of IL-17 mRNA in healed mucosa, adjusted for age, gender and CRP, generated through the Cox model. Cut-off for normalization was defined by the upper bound of mean $\Delta C_T$ values in the control patients.

We performed survival analyses (Cox-regression) for the categories of cytokine expression levels in healed mucosa. Higher levels of TNF-α and IFN-yγ expression were significantly associated with relapses within 18 months (HR=2.2, p=0.04, HR=2.5, p=0.03, respectively). Normalization of IL-17 tended to predict long-term remission, with a p value of 0.1. Survival plots from the Cox regression models are presented in FIGS. 2 to 4.

ROC Analysis

Tertile-based cut-off values resulted in following test characteristics: Lowest tertile of IL-17 gene expression level predicted remission with the sensitivity of 47.5% and specificity of 75% (Area under curve (AUC) 0.72, 95 CI 0.56-0.86, p=0.013). The sensitivity was 85% and specificity 40% (AUC 0.65, 95 CI 0.50-0.81, p=0.06) for low TNF-a mRNA expression. In low IFN-gamma the sensitivity was 80% and specificity 40% (AUC 0.67, 95 CI 0.51-0.84, p=0.06). For IL-17, selection of a cut-off that would increase the sensitivity to above 90% resulted in specificity of IL-17 of only 32%, for TNF-a a sensitivity of over 90% results in specificity of 30%, and for IFN-gamma a sensitivity of over 90% results in specificity of 36%.

Conclusion

We have demonstrated an association between post treatment gene expression levels of TH17 and TH1 related cytokines and sustained remission after anti TNFα therapy in patients with ulcerative colitis. Low mucosal gene expression levels of interleukin-17 and TNF-α resulted in increased odds of sustained clinical and endoscopic remission defined by the UCDAI. Normalization of mucosal TH1 cytokines, as IFN-gamma, TNF-α and interleukin-17 may be important criteria in the evaluation of when to stop treatment with Infliximab.

The invention claimed is:

1. A method of assaying whether a patient with inflammatory bowel disease (IBD) and who has been treated with an anti TNFα antibody is in immunological remission (IR) comprising
    assaying a GI mucosal sample from said patient for the expression level of TNFα,
    detecting the expression level of TNFα in said sample using PCR or an immunological assay,
    wherein the detected expression level of TNFα is not normalized relative to a control and thus the patient is not in IR, treating the patient with continued anti-TNFα antibodies;
    wherein the detected expression level of TNFα is normalized relative to a control and thus the patient is in IR, ceasing treatment with TNFα antibodies.

2. The method of claim 1 wherein the level of at least one further cytokine is determined.

3. The method of claim 1 wherein said patient has ulcerative colitis (UC).

4. The method of claim 3 further comprising detecting the expression level of IFNγ.

5. The method of claim 3 wherein said patient has an Ulcerative Colitis Disease Activity Index (UCDAI) score of 3 points or lower.

6. The method of claim 1 wherein said patient is in endoscopic remission.

7. The method of claim 1 wherein said patient has been treated with certolizumab, golimumab, infliximab, or adalimumab.

8. The method of claim 1 wherein said patient is human.

9. The method of claim 1 wherein the expression level of TNF-α in the GI mucosal sample of said patient is not normalized and said treatment is continued, said method further comprising repeating the method of claim 1 and discontinuing treatment if the expression level of TNF-α in the GI mucosal sample of said patient is normalized and continuing treatment if the expression level of TNF-α in the GI mucosal sample of said patient is not normalized.

10. The method of claim 1 wherein detecting the expression level of TNF-α is carried out by detecting the level of nucleic acid encoding TNF-α.

11. The method of claim 10 wherein detecting the expression level of TNF-α is carried out by PCR.

12. The method of claim 1 wherein detecting the expression level of TNF-α is carried out by detection of TNF-α at the protein level.

13. The method of claim 12 wherein detecting the expression level of TNF-α is carried out by an ELISA or RIA based assay.

* * * * *

SEQUENCE LISTING

```
<160> NUMBER OF SEQ ID NOS: 18

<210> SEQ ID NO 1
<211> LENGTH: 25
<212> TYPE: PRT
<213> ORGANISM: Artificial Sequence
<220> FEATURE:
<223> OTHER INFORMATION: human TNFa fragment

<400> SEQUENCE: 1

Glu Thr Pro Glu Gly Ala Glu Ala Lys Pro Trp Tyr Glu Pro Ile Tyr
1               5                   10                  15

Leu Gly Gly Val Phe Gln Leu Glu Lys
            20                  25

<210> SEQ ID NO 2
<211> LENGTH: 25
<212> TYPE: PRT
<213> ORGANISM: Artificial Sequence
<220> FEATURE:
<223> OTHER INFORMATION: TNFa fragment

<400> SEQUENCE: 2
```

```
Thr Pro Ser Asp Lys Pro Val Ala His Val Val Ala Asn Pro Gln Ala
1               5                   10                  15

Glu Gly Gln Leu Gln Trp Leu Asn Arg
            20                  25

<210> SEQ ID NO 3
<211> LENGTH: 12
<212> TYPE: PRT
<213> ORGANISM: Artificial Sequence
<220> FEATURE:
<223> OTHER INFORMATION: TNFa fragment

<400> SEQUENCE: 3

Ala Asn Ala Leu Leu Ala Asn Gly Val Glu Leu Arg
1               5                   10

<210> SEQ ID NO 4
<211> LENGTH: 19
<212> TYPE: DNA
<213> ORGANISM: Artificial Sequence
<220> FEATURE:
<223> OTHER INFORMATION: TNFa forward primer

<400> SEQUENCE: 4
cacgctcttc tgcctgctg                                              19

<210> SEQ ID NO 5
<211> LENGTH: 20
<212> TYPE: DNA
<213> ORGANISM: Artificial Sequence
<220> FEATURE:
<223> OTHER INFORMATION: TNFa reverse primer

<400> SEQUENCE: 5
gatgatctga ctgcctgggc                                             20

<210> SEQ ID NO 6
<211> LENGTH: 25
<212> TYPE: DNA
<213> ORGANISM: Artificial Sequence
<220> FEATURE:
<223> OTHER INFORMATION: TNFa probe

<400> SEQUENCE: 6
ccagagggaa gagttcccca gggac                                       25

<210> SEQ ID NO 7
<211> LENGTH: 24
<212> TYPE: DNA
<213> ORGANISM: Artificial Sequence
<220> FEATURE:
<223> OTHER INFORMATION: IL-17 forward primer

<400> SEQUENCE: 7
tgattggaag aaacaacgat gact                                        24

<210> SEQ ID NO 8
<211> LENGTH: 24
<212> TYPE: DNA
<213> ORGANISM: Artificial Sequence
<220> FEATURE:
<223> OTHER INFORMATION: IL-17 reverse primer

<400> SEQUENCE: 8
attgtgattc ctgccttcac tatg                                        24
```

<210> SEQ ID NO 9
<211> LENGTH: 26
<212> TYPE: DNA
<213> ORGANISM: Artificial Sequence
<220> FEATURE:
<223> OTHER INFORMATION: IL-17 probe

<400> SEQUENCE: 9
tggtgtcact gctactgctg ctgagc                                    26

<210> SEQ ID NO 10
<211> LENGTH: 20
<212> TYPE: DNA
<213> ORGANISM: Artificial Sequence
<220> FEATURE:
<223> OTHER INFORMATION: IL-23A forward primer

<400> SEQUENCE: 10
cccaaggact cagggacaac                                           20

<210> SEQ ID NO 11
<211> LENGTH: 26
<212> TYPE: DNA
<213> ORGANISM: Artificial Sequence
<220> FEATURE:
<223> OTHER INFORMATION: IL-23A reverse primer

<400> SEQUENCE: 11
tcctagcagc ttctcataaa aaatca                                    26

<210> SEQ ID NO 12
<211> LENGTH: 28
<212> TYPE: DNA
<213> ORGANISM: Artificial Sequence
<220> FEATURE:
<223> OTHER INFORMATION: IL-23A probe

<400> SEQUENCE: 12
tcagttctgc ttgcaaagga tccaccag                                  28

<210> SEQ ID NO 13
<211> LENGTH: 20
<212> TYPE: DNA
<213> ORGANISM: Artificial Sequence
<220> FEATURE:
<223> OTHER INFORMATION: IL-6 forward primer

<400> SEQUENCE: 13
ccaggagccc agctatgaac                                           20

<210> SEQ ID NO 14
<211> LENGTH: 19
<212> TYPE: DNA
<213> ORGANISM: Artificial Sequence
<220> FEATURE:
<223> OTHER INFORMATION: IL-6 reverse primer

<400> SEQUENCE: 14
cccagggaga aggcaactg                                            19

<210> SEQ ID NO 15
<211> LENGTH: 19
<212> TYPE: DNA
<213> ORGANISM: Artificial Sequence
<220> FEATURE:

```
<223> OTHER INFORMATION: IL-6 probe

<400> SEQUENCE: 15
cccagggaga aggcaactg                                                    19

<210> SEQ ID NO 16
<211> LENGTH: 24
<212> TYPE: DNA
<213> ORGANISM: Artificial Sequence
<220> FEATURE:
<223> OTHER INFORMATION: TGFb forward primer

<400> SEQUENCE: 16
ctgctgaggc tcaagttaaa agtg                                              24

<210> SEQ ID NO 17
<211> LENGTH: 21
<212> TYPE: DNA
<213> ORGANISM: Artificial Sequence
<220> FEATURE:
<223> OTHER INFORMATION: TGFb reverse primer

<400> SEQUENCE: 17
tgaggtatcg ccaggaattg t                                                 21

<210> SEQ ID NO 18
<211> LENGTH: 30
<212> TYPE: DNA
<213> ORGANISM: Artificial Sequence
<220> FEATURE:
<223> OTHER INFORMATION: TGFb probe

<400> SEQUENCE: 18
cagcacgtgg agctgtacca gaaatacagc                                        30
```